(12) United States Patent
Walker et al.

(10) Patent No.: US 8,818,064 B2
(45) Date of Patent: Aug. 26, 2014

(54) TIME-DOMAIN ESTIMATOR FOR IMAGE RECONSTRUCTION

(75) Inventors: William F. Walker, Charlottesville, VA (US); Michael Ellis, Landenberg, PA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 114 days.

(21) Appl. No.: 13/380,224

(22) PCT Filed: Jun. 25, 2010

(86) PCT No.: PCT/US2010/040054
§ 371 (c)(1),
(2), (4) Date: Mar. 9, 2012

(87) PCT Pub. No.: WO2010/151809
PCT Pub. Date: Dec. 29, 2010

(65) Prior Publication Data
US 2012/0163691 A1    Jun. 28, 2012

Related U.S. Application Data

(60) Provisional application No. 61/220,813, filed on Jun. 26, 2009, provisional application No. 61/356,908, filed on Jun. 21, 2010.

(51) Int. Cl.
*G06K 9/00* (2006.01)
*A61B 8/00* (2006.01)

(52) U.S. Cl.
USPC .......................... 382/131; 600/437; 600/443

(58) Field of Classification Search
USPC .......... 382/128–134; 600/407, 425, 437, 443, 600/447, 459; 128/920, 922
See application file for complete search history.

(56) References Cited

U.S. PATENT DOCUMENTS

| 5,546,360 | A  | 8/1996 | Deegan |
| 6,242,743 | B1 | 6/2001 | DeVito et al. |
| 6,398,733 | B1 | 6/2002 | Simopoulos et al. |

(Continued)

FOREIGN PATENT DOCUMENTS

| WO | WO-2007035765 A2 | 3/2007 |
| WO | WO-2007035765 A3 | 3/2007 |
| WO | WO-2010151809 A1 | 12/2010 |

OTHER PUBLICATIONS

"International Application Serial No. PCT/US10/40054, Search Report mailed Aug. 23, 2010", 4 pgs.

(Continued)

*Primary Examiner* — Abolfazl Tabatabai
(74) *Attorney, Agent, or Firm* — Schwegman Lundberg & Woessner, P.A.

(57) ABSTRACT

One or more systems, methods, or computer program products can include receiving an echo data set including information representative of an echo sensed by a transducer, provided at least in part by one or more actual targets included in a region of interest. The region of interest can be modeled, including selecting or generating an array manifold matrix including information corresponding to any one or more candidate targets. The weights of the candidate targets can be determined using the array manifold matrix and the echo data set, including minimizing an argument of a function modeling the weights of the candidate targets. In an example, the echo data set can be dithered, such as by adding a specified dithering signal.

38 Claims, 15 Drawing Sheets

(56) References Cited

U.S. PATENT DOCUMENTS

| | | | |
|---|---|---|---|
| 6,501,747 B1 | 12/2002 | Friedlander et al. | |
| 6,579,238 B1 * | 6/2003 | Simopoulos et al. | 600/443 |
| 6,692,439 B1 * | 2/2004 | Walker et al. | 600/443 |
| 7,402,136 B2 | 7/2008 | Hossack et al. | |
| 7,699,766 B2 | 4/2010 | Ellsworth et al. | |
| 7,750,537 B2 | 7/2010 | Hossack et al. | |
| 7,822,119 B2 | 10/2010 | Boon et al. | |
| 8,057,392 B2 | 11/2011 | Hossack et al. | |
| 8,121,354 B2 | 2/2012 | Nagasaka et al. | |
| 2003/0133601 A1 | 7/2003 | Giger et al. | |
| 2006/0058666 A1 | 3/2006 | Tanigawa | |
| 2007/0016022 A1 | 1/2007 | Blalock et al. | |
| 2007/0057671 A1 | 3/2007 | Nezafat et al. | |
| 2010/0142781 A1 | 6/2010 | Walker et al. | |
| 2010/0256952 A1 * | 10/2010 | Dekker | 702/180 |
| 2010/0331686 A1 * | 12/2010 | Hossack et al. | 600/439 |

OTHER PUBLICATIONS

"International Application Serial No. PCT/US10/40054, Written Opinion mailed Aug. 23, 2010", 8 pgs.
"International Application Serial No. PCT/US2010/040054, International Preliminary Report on Patentability mailed Jan. 12, 2012", 10 pgs.
Bethel, R, et al., "Single Snapshot Spatial Processing: Optimized and Constrained", Sensor Array and Multichannel Signal Processing Workshop Proceedings. IEEE, (2002), 508-512.
Ellis, Michael A, et al., "Super-Resolution Image Reconstruction With Reduced Computational Complexity", 2009 IEEE International Ultrasonics Symposium Proceedings, (2009), 2351-2354.
Mann, et al., "A Constrained Adaptive Beamformer for Medical Ultrasound", Ultrasonics Symposium. Proceedings. IEEE. p. 1807 Oct. 2002, col. 2, para 4; p. 1808, coil . para 1-2. Fig. 3, (Oct. 11, 2002), p. 1807-1810.
Viola, et al., "Time-Domain Optimized Near-Field Estimator for Ultrasound Imaging : Initial 1-40", IEEE Transactions on Medical Imaging 27(1), (Jan. 2008), 99-110.
"U.S. Appl. No. 11/992,368, Corrected Notice of Allowability mailed Nov. 8, 2013", 2 pgs.
"U.S. Appl. No. 11/992,368, Non Final Office Action mailed Jan. 4, 2013", 10 pgs.
"U.S. Appl. No. 11/992,368, Notice of Allowance mailed Feb. 4, 2014", 5 pgs.
"U.S. Appl. No. 11/992,368, Notice of Allowance mailed Sep. 27, 2013", 10 pgs.
"U.S. Appl. No. 11/992,368, Preliminary Amendment filed on Mar. 31, 2010", 3 pgs.
"U.S. Appl. No. 11/992,368, Response filed Jun. 4, 2013 to Non Final Office Action mailed Jan. 4, 2013", 15 pgs.
"European Application Serial No. 06814967, Response Filed Oct. 15, 2010 to Office Action mailed Jun. 16, 2010", 22 pgs.
"European Application Serial No. 06814967.3, Examination Notification Art. 94(3) mailed Mar. 8, 2013", 5 pgs.
"European Application Serial No. 06814967.3, Extended European Search Report mailed Mar. 5, 2010", 3 pgs.
"European Application Serial No. 06814967.3, Office Action mailed Mar. 23, 2010", 5 pgs.
"European Application Serial No. 06814967.3, Office Action mailed Jun. 16, 2010", 1 pgs.
"International Application Serial No. PCT/US2006/036536, International Preliminary Report on Patentability mailed Mar. 26, 2008", 5 pgs.
"International Application Serial No. PCT/US2006/036536, Written Opinion mailed May 15, 2007", 4 pgs.
Lo, F, et al., "Adaptive Array Processing for Wide-Band Action Sonars", IEEE Journal of Oceanic Engineering. vol. 29, No. 3, (Jul. 2004), 837-846.
Viola, F., et al., "Adaptive Signal Processing in Medical Ultrasound Beamforming", Ultrasonics Symposium, IEEE. vol. 4, (Sep. 21, 2005), 18-21.

* cited by examiner

TIME-DOMAIN ESTIMATOR FOR IMAGE RECONSTRUCTION

STATEMENT REGARDING FEDERALLY SPONSORED RESEARCH OR DEVELOPMENT

This invention was made with government support under award number NIH 126509-101-GC11470-3135 from the National Institute of Health. The government has certain rights in this invention.

CLAIM OF PRIORITY

This patent application is a U.S. National Stage Filing under 35 U.S.C. 371 from International Patent Application Serial No. PCT/US2010/040054, filed Jun. 25, 2010 and published on Dec. 29, 2010 as WO 2010/151809 A1, which claims the benefit of priority to U.S. Provisional Patent Application Ser. No. 61/220,813, entitled "Method, System, and Computer Program Product for Ultrasound," filed on Jun. 26, 2009, and to U.S. Provisional Patent Application Ser. No. 61/356,908, entitled "Method, System, and Computer Program Product for Ultrasound," filed on Jun. 21, 2010, the benefit of priority to each of which is hereby presently claimed, and the contents of each of which are herein incorporated by reference in their respective entireties.

CROSS-REFERENCE TO RELATED PATENT DOCUMENTS

The following documents are hereby incorporated by reference herein in their respective entireties:
1. U.S. patent application Ser. No. 11/992,368, "System and Method for Adaptive Beamforming for Image Reconstruction and/or Target/Source Localization" (Walker et al.), filed Mar. 18, 2008, including its disclosure of reconstruction of target locations and amplitudes using signals received from one or more real targets in space, the signals represented by a time-domain data vector, such as received in the near-field of a transducer array;
2. U.S. patent application Ser. No. 12/467,216, "Reduction of Echo Decorrelation Facilitating Motion Estimation" (Walker et al.), filed May 15, 2009, including its disclosure of using principal components analysis to extract information about a moving target;
3. U.S. patent application Ser. No. 11/840,079, "Hybrid Dual Layer Diagnostic Ultrasound Transducer Array" (Hossack et al.), filed Aug. 16, 2007, including its disclosure of a hybrid ultrasonic transducer element array including one or more commonly-shared piezoelectric or conductive regions;
4. U.S. patent application Ser. No. 12/371,911, "Imaging or Communications System Utilizing Multisample Apodization and Method" (Walker et a.), filed Feb. 16, 2009, including its disclosure of using finite impulse response filtering of channel data received from a transducer array using tap weights calculated at least in part as a function of distance of the array from an object being imaged;
5. U.S. patent application Ser. No. 11/906,614, "Method, System and Computer Program Product for Registration of Multi-Dimensional Datasets" (Walker et al.), filed Oct. 2, 2007, including its disclosure of estimating changes in an object represented by multiple datasets using a piece-wise representation of a first dataset;
6. U.S. patent application Ser. No. 11/245,266, "Efficient Architecture for 3D and Planar Ultrasonic Imaging—Synthetic Axial Acquisition and Method" (Hossack et al.), filed Oct. 5, 2005, including its disclosure of combining data gathered, over numerous transmit and receive echo cycles or iterations, into a synthetic acquisition representing a complete echo characteristic acquisition;
7. U.S. Pat. No. 7,402,136, "Efficient Ultrasound System for Two-Dimensional C-Scan Imaging and Related Method Thereof" (Hossack et al.), issued Jul. 22, 2008, including its disclosure of forming images representing three dimensional regions using a time-serial beamforming technique on data received from a two-dimensional transducer array;
8. U.S. patent application Ser. No. 11/160,915, "Ultrasound Imaging Beam-Former Apparatus and Method" (Blalock et al.), filed Jul. 14, 2005, including its disclosure of beamforming using both in-phase and quadrature sampling of an incoming signal received from a transducer (e.g., to provide a complex received signal including both magnitude and phase information);
9. U.S. patent application Ser. No. 11/160,914, "Ultrasonic Transducer Drive" (Blalock et al.), filed Jul. 14, 2005, including its disclosure of apparatus of techniques of driving a transducer, such as an ultrasound transducer, to provide acoustic or mechanical pulses from which echoes can be received, such as for use in an imaging system;
10. U.S. patent application Ser. No. 10/506,722, "Intuitive Ultrasonic Imaging System and Related Method Thereof" (Walker et al.), filed Sep. 7, 2004, including its disclosure of a hand-held ultrasonic imaging unit such as including a two-dimensional array of transducers; and
11. U.S. Pat. No. 6,692,439, "Angular Scatter Imaging System Using Translating Apertures and Method Thereof" (Walker et al.), issued Feb. 17, 2004, including its disclosure of an imaging system and techniques for imaging angular scatter, such as including use of translating apertures to impose stability in the speckle pattern allowing comparison of echoes acquired at different scattering angles.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2010, University of Virginia Patent Foundation (UVAPF). All Rights Reserved.

BACKGROUND

Ultrasound occupies an important role in cardiac, fetal, and breast imaging, among other applications. For example, ultrasound's real-time nature and lack of ionizing radiation can make it more attractive than other alternatives. Unfortunately, high levels of image clutter can present a significant problem for certain patients, and diffraction effects can limit spatial resolution (e.g., to no better than hundreds of microns). For example, three-dimensional dynamic focusing can be needed to approach the predicted theoretical diffraction limit. Such focusing can unacceptably increase cost and complexity of the imaging system.

Generally, the resolution limit for ultrasound is assumed to be no better than $\lambda z/D$, where $\lambda$ can represent the ultrasound acoustic wavelength, $z$ can represent the range to a target to be imaged, and $D$ can represent an aperture size corresponding to the ultrasonic transducer. Thus, at least two routes can be used to improve resolution. The first can be to increase the operating frequency and thereby reduce the wavelength, λ. Such wavelength reduction works well at shallow depths, but can be limited by frequency dependent attenuation as the depth of the region of interest is increased. As the operating frequency increases, the signal to noise ratio (SNR) can also decrease, until it falls too low to form useful images. In one approach, coded excitation can mitigate this effect, but a tradeoff between resolution and SNR still exists. In another approach, resolution can be increased by expanding the imaging aperture, at least up to the point where an f-number (e.g., z/D) approaches 0.5.

While aperture growth can be broadly effective, a practical limit can exist since the aperture cannot be made unreasonably large. Research over the past decade has shown that resolution in vivo does not necessarily scale with aperture growth as predicted. This effect is believed to result from phase aberration. For example, as larger apertures are employed, the effect of phase aberration can become more significant. Moreover, for many organs the anatomical acoustic window may not be large enough to allow f/0.5 imaging. For example, in heart imaging, the space between the ribs can limit useable aperture size.

Aperture growth in elevation can also have only limited value in linear and phased arrays that use a fixed lens for elevation focusing. For example, a larger aperture in elevation can improve resolution at the focus, but it can also degrade resolution elsewhere. In another approach, if the active aperture size is increased while maintaining element spatial sampling, then a channel count used for the imaging system may grow exorbitantly. This is especially true when 1.5D or 2D arrays are employed for elevation focusing.

The past decade has seen 2D arrays progress from research curiosities to common clinical tools. The majority of 2D array applications have been in cardiology where there is a need for rapid volume acquisition. Such 2D array systems can include 2,500 active elements or more, and can include integrated circuitry within the probe assembly. Such 2D arrays can use sub-array beamforming techniques, but such methods generally limit resolution and contrast to below theoretical limits.

Extending these approaches to breast imaging can also present major challenges. For example, the operating frequency in the breast can be substantially higher. Given the spatial sampling requirements of conventional beamforming (CBF) this might entail a quadrupling (doubling in each dimension) of channel count for a similarly-sized transducer as would be used for a cardiac imaging application. Also, to approach diffraction limited resolution, a 2D array for breast imaging can be twice as large in each dimension as compared to cardiac imaging. Thus to a crude degree, a 2D array based breast imager can be roughly 16 times the elements and channels of existing 2D arrays. Generally, cardiac 2D arrays have costs that can exceed tens of thousands of dollars, so a 2D array based breast scanner might not be commercially viable, unless channel count or array size can be reduced.

OVERVIEW

Ultrasonic imaging can be applied in a broad array of clinical arenas such as including breast imaging, cardiac imaging, or in obstetrics and gynecology, among others. In each of these areas, ultrasound's real-time nature, lack of ionizing radiation, and relative comfort for the patient can make it an attractive choice. Diagnosis and screening has been improved through the application of speckle reduction (via compounding and image processing). The transition to 1.5D and 2D transducer arrays for improved focusing can further improve diagnostic utility. In one approach, delay-and-sum beamformers can achieve a diffraction-limited resolution on the order of hundreds of microns (e.g., hundreds of micrometers). Background clutter, possibly due to strong off-axis scattering, can degrade image quality provided by such delay-and-sum beamformers.

Example 1 can include subject matter such as a method, a means for performing acts, or a machine-readable medium including instructions that, when performed by the machine, cause the machine to perform acts including receiving an echo data set including information representative of an echo provided at least in part by one or more actual targets included in a region of interest, modeling the region of interest, the modeling including selecting or generating an array manifold matrix, the array manifold matrix including information corresponding to any one or more candidate targets included in the region of interest, determining weights of the candidate targets using the array manifold matrix and the echo data set. In an example the determining the weights can include minimizing an argument of a function modeling the weights of the candidate targets, the minimizing subject to a constraint that a product of the array manifold matrix and a vector representation of the determined weights of each of the one or more candidate targets is about equal to the received echo data set corresponding to the one or more actual targets.

In Example 2, the subject matter of Example 1 can optionally include a function modeling the weights of the candidate targets comprising an exponential function.

In Example 3, the subject matter of one or any combination of Examples 1-2 can optionally include a function modeling the weights of the candidate targets comprising a joint Gaussian probability density function.

In Example 4, the subject matter of one or any combination of Examples 1-3 can optionally include minimizing the argument comprising minimizing a product of (1) a Hermitian transpose of the vector representing the weights of each of the one or more candidate targets, (2) the inverse of a covariance matrix determined using a vector representation of the weights of each of the one or more candidate targets, and (3) the vector representation of the weights of each of the one or more candidate targets.

In Example 5, the subject matter of one or any combination of Examples 1-4 can optionally include determining weights of the one or more candidate targets comprising performing a singular value decomposition of the array manifold matrix and transforming the echo data set using an inverse of a matrix provided by the singular value decomposition of the array manifold matrix.

In Example 6, the subject matter of one or any combination of Examples 1-5 can optionally include constructing an image representing an estimate of one or more of the actual target locations using the determined weights of the one or more candidate targets.

In Example 7, the subject matter of one or any combination of Examples 1-6 can optionally include a brightness of a particular location in the image determined at least in part using the determined weights of the one or more candidate targets.

In Example 8, the subject matter of one or any combination of Examples 1-7 can optionally include a region of interest includes a tissue region, the echo data set including information representative of ultrasonic energy scattered or reflected by the one or more actual targets and received by an ultrasonic transducer, wherein one or more of the actual target locations are within the tissue region.

In Example 9, the subject matter of one or any combination of Examples 1-8 can optionally include an array manifold matrix comprising information corresponding to one or more crisply-modeled candidate targets.

In Example 10, the subject matter of one or any combination of Examples 1-9 can optionally an array manifold matrix comprising information corresponding to one or more diffusely-modeled candidate targets.

In Example 11, the subject matter of one or any combination of Examples 1-10 can optionally include determining the weights of the candidate targets including subdividing the region of interest spatially into a full-solution region, and a region outside the full-solution region, wherein the selecting or generating the array manifold matrix includes reducing a rank of a portion of the array manifold matrix corresponding to the region outside the full solution region.

In Example 12, the subject matter of one or any combination of Examples 1-11 can optionally include determining the weights of the candidate target locations including subdividing the region of interest spatially into a first full-solution region, and a second full-solution region, wherein the weights of one or more candidate targets included in the first full-solution region are determined at least in part using a first processor, and wherein the weights of one or more candidate targets included in the second full-solution region are determined at least in part using a second processor.

In Example 13, the subject matter of one or any combination of Examples 1-12 can optionally include determining the weights of the candidate target locations including subdividing the echo data set temporally, the subdividing including providing a subset of the echo data set, the subset including a first interval corresponding to a first portion of the region of interest from which corresponding echo data has not been truncated, and the subset including a second interval corresponding to a second portion of the region of interest from which corresponding echo data is truncated, and wherein the first and second intervals overlap in time.

In Example 14, the subject matter of one or any combination of Examples 1-13 can optionally include adding a first specified dithering signal to the echo data set to provide a first dithered echo data set, adding a second specified dithering signal to the echo data set to provide a second dithered echo data set, wherein the determining the weights of the candidate target locations includes determining a first vector representing the weights of the candidate target locations using the first dithered echo data set, and determining a second vector representing the weights of the candidate target locations using the second dithered echo data set.

In Example 15, the subject matter of one or any combination of Examples 1-14 can optionally include constructing an image representing an estimate of one or more of the actual target locations using the determined weights of the one or more candidate targets, wherein a brightness of a particular location in the image is determined at least in part using a determined weight of one or more candidate targets included in the first vector, and a determined weight of one or more candidate targets included in the second vector.

In Example 16, the subject matter of one or any combination of Examples 1-15 can optionally include a brightness of a particular location in the image determined using one or more of a central tendency of a combination, a maximum, a minimum, or a specified range of values of the determined weight of one or more candidate targets included in the first vector, and the determined weight of one or more candidate targets included in the second vector.

In Example 17, the subject matter of one or any combination of Examples 1-16 can optionally include first and second specified dithering signals represented by information included in respective first and second specified dithering vectors, and wherein the first and second dithering vectors are orthogonal to each other.

In Example 18, the subject matter of one or any combination of Examples 1-17 can optionally include at least one of the first or second dithering vectors being non-random.

In Example 19 can include, or can optionally be combined with subject matter of one or any combination of Examples 1-18, subject matter (such as a system or other apparatus) comprising a processor and a processor-readable medium, the processor-readable medium comprising instructions that, when performed by the processor, cause the system to receive an echo data set including information representative of an echo provided at least in part by one or more actual targets included in a region of interest, model the region of interest, including instructions that cause the system to select or generate an array manifold matrix, the array manifold matrix including information corresponding to any one or more candidate targets included in the region of interest, determine weights of the candidate targets using the array manifold matrix and the echo data set. In an example, the instructions can include instructions that cause the system to minimize an argument of a function modeling the weights of the candidate targets, the minimizing subject to a constraint that a product of the array manifold matrix and a vector representation of the determined weights of each of the one or more candidate targets is about equal to the received echo data set corresponding to the one or more actual targets.

In Example 20, the subject matter of Example 19 can optionally include a function modeling weights of the candidate targets comprising an exponential function.

In Example 21, the subject matter of one or any combination of Examples 19-20 can optionally include a function modeling the weights of the candidate targets comprising a joint Gaussian probability density function.

In Example 22, the subject matter of one or any combination of Examples 19-21 can optionally include instructions to minimize a product of (1) a Hermitian transpose of the vector representing the weights of each of the one or more candidate targets, (2) the inverse of a covariance matrix determined using a vector representation of the weights of each of the one or more candidate targets, and (3) the vector representation of the weights of each of the one or more candidate targets.

In Example 23, the subject matter of one or any combination of Examples 19-22 can optionally include instructions to determine the weights of the one or more candidate targets, including instructions to perform a singular value decomposition of the array manifold matrix, and transform the echo data set using an inverse of a matrix provided by the singular value decomposition of the array manifold matrix.

In Example 24, the subject matter of one or any combination of Examples 19-23 can optionally include instructions to reconstruct an image representing an estimate of one or more of the actual target locations using the determined weights of the one or more candidate targets.

In Example 25, the subject matter of one or any combination of Examples 19-24 can optionally include instructions to determine a brightness of a particular location in the image at least in part using the determined weights of the one or more candidate targets.

In Example 26, the subject matter of one or any combination of Examples 19-25 can optionally include a region of interest comprising a tissue region, wherein the echo data set includes information representative of ultrasonic energy scattered or reflected by the one or more actual targets and received by an ultrasonic transducer array, wherein one or more of the actual target locations are within the tissue region.

In Example 27, the subject matter of one or any combination of Examples 19-26 can optionally include an array manifold matrix comprising information corresponding to one or more crisply-modeled candidate targets.

In Example 28, the subject matter of one or any combination of Examples 19-27 can optionally include an array manifold matrix comprising information corresponding to one or more diffusely-modeled candidate targets.

In Example 29, the subject matter of one or any combination of Examples 19-28 can optionally include instructions to determine the weights of the candidate target locations including instructions to subdivide the region of interest spatially into a full-solution region, and a region outside the full-solution region, wherein the instructions to select or generate the array manifold matrix include instructions to reduce a rank of a portion of the array manifold matrix corresponding to the region outside the full solution region.

In Example 30, the subject matter of one or any combination of Examples 19-29 can optionally include instructions to determine the weights of the candidate target locations including instructions to subdivide the region of interest spatially into a first full-solution region, and a second full-solution region, wherein the system comprises a first processor configured to determine, at least in part, the weights of one or more candidate targets included in the first full-solution region, and wherein the system comprises a second processor configured to determine, at least in part, the weights of one or more candidate targets included in the second full-solution region.

In Example 31, the subject matter of one or any combination of Examples 19-30 can optionally include instructions to determine the weights of the candidate target locations include instructions to subdivide the echo data set temporally, including instructions to provide a subset of the echo data set, the subset including a first interval corresponding to a first portion of the region of interest from which corresponding echo data has not been truncated, and the subset including a second interval corresponding to a second portion of the region of interest from which corresponding echo data is truncated, wherein the first and second intervals overlap in time.

In Example 32, the subject matter of one or any combination of Examples 19-31 can optionally include instructions to add a first specified dithering signal to the echo data set to provide a first dithered echo data set, add a second specified dithering signal to the echo data set to provide a second dithered echo data set, wherein the instructions causing the system to determine the weights of the candidate target locations include instructions to determine a first vector representing the weights of the candidate target locations using the first dithered echo data set, and determine a second vector representing the weights of the candidate target locations using the second dithered echo data set.

In Example 33, the subject matter of one or any combination of Examples 19-32 can optionally include instructions to reconstruct an image representing an estimate of one or more of the actual target locations using the determined weights of the one or more candidate targets, wherein a brightness of a particular location in the image is determined at least in part using a determined weight of the one or more candidate targets included in the first vector, and a determined weight of the one or more candidate targets included in the second vector.

In Example 34, the subject matter of one or any combination of Examples 19-33 can optionally include a brightness of a particular location in the image determined using one or more of a central tendency of a combination, a maximum, a minimum, or a specified range of values of the determined weight of one or more candidate targets included in the first vector, and the determined weight of one or more candidate targets included in the second vector.

In Example 35, the subject matter of one or any combination of Examples 19-34 can optionally include first and second specified dithering signals represented by information included in respective first and second specified dithering vectors, wherein the first and second dithering vectors are orthogonal to each other.

In Example 36, the subject matter of one or any combination of Examples 19-35 can optionally include at least one of the first or second dithering vectors being non-random.

Example 37 can include, or can optionally be combined with the subject matter of one or any combination of Examples 1-36 to include, subject matter such as a method, a means for performing acts, or a machine-readable medium including instructions that, when performed by the machine, cause the machine to perform acts, including receiving an echo data set including information representative of an echo provided at least in part by one or more actual targets included in a region of interest, modeling the region of interest, the modeling including selecting or generating an array manifold matrix, the array manifold matrix including information corresponding to any one or more candidate targets included in the region of interest, adding a first specified dithering signal to the echo data set to provide a first dithered echo data set, adding a second specified dithering signal to the echo data set to provide a second dithered echo data set, determining weights of the candidate targets using the array manifold matrix and the echo data set, the determining the weights subject to a constraint that a product of the array manifold matrix and a vector representation of the determined weights of each of the one or more candidate targets is about equal to the received echo data set corresponding to the one or more actual targets. In an example, the determining the weights of the candidate target locations includes determining a first vector representing the weights of the candidate target locations using the first dithered echo data set, and determining a second vector representing the weights of the candidate target locations using the second dithered echo data set.

In Example 38, the subject matter of Example 37 can optionally include constructing an image representing an estimate of one or more of the actual target locations using the determined weights of the one or more candidate targets, wherein a brightness of a particular location in the image is determined at least in part using a determined weight of one or more candidate targets included in the first vector, and a determined weight of one or more candidate targets included in the second vector.

In Example 39 can include, or can optionally be combined with subject matter of one or any combination of Examples 1-38, subject matter (such as a system or other apparatus) comprising a processor and a processor-readable medium, the processor-readable medium comprising instructions that, when performed by the processor, cause the system to receive an echo data set including information representative of an echo provided at least in part by one or more actual targets included in a region of interest, model the region of interest, including instructions that cause the system to select or generate an array manifold matrix, the array manifold matrix including information corresponding to any one or more candidate targets included in the region of interest, determine weights of the candidate targets using the array manifold matrix and the echo data set, subject to a constraint that a product of the array manifold matrix and a vector representation of the determined weights of each of the one or more candidate targets is about equal to the received echo data set corresponding to the one or more actual targets, add a first specified dithering signal to the echo data set to provide a first dithered echo data set, add a second specified dithering signal to the echo data set to provide a second dithered echo data set. In an example, the instructions causing the system to determine the weights of the candidate target locations include instructions to determine a first vector representing the weights of the candidate target locations using the first dithered echo data set, and determine a second vector representing the weights of the candidate target locations using the second dithered echo data set.

In Example 40, the subject matter of Example 39 can optionally include instructions that cause the system to reconstruct an image representing an estimate of one or more of the actual target locations using the determined weights of the one or more candidate targets, a brightness of a particular location in the image determined at least in part using a determined weight of the one or more candidate targets included in the first vector, and a determined weight of the one or more candidate targets included in the second vector.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
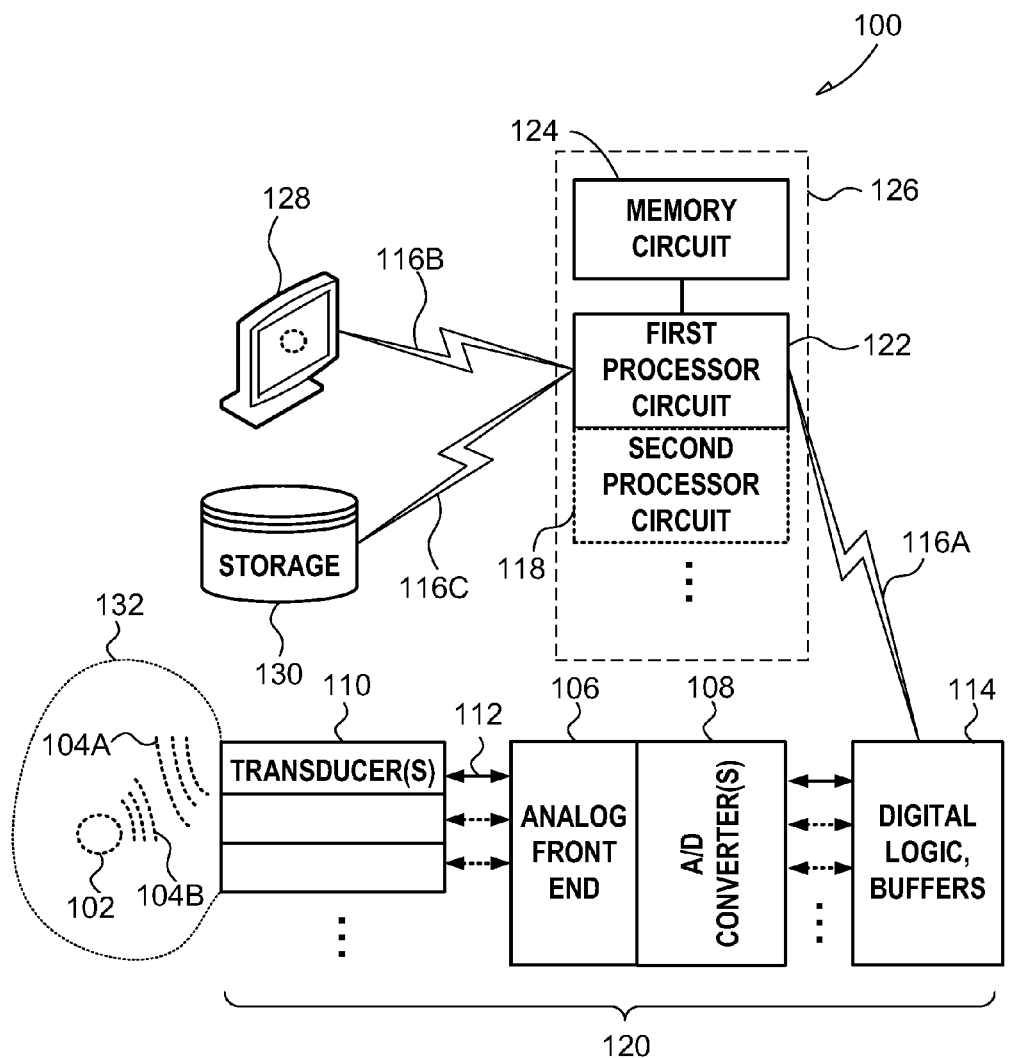
FIG. 1 illustrates generally an example of a system that can include one or more processors, the system configured to receive a time-domain echo data set from one or more transducers.

RADAR and SONAR researchers have applied adaptive beamforming (ABF), such as to null off-axis scatterers, to exceed a theoretically-determined diffraction limit, or to reduce transducer and signal-processing "front-end" complexity. ABF can be used to optimize beamformer parameters such as for specific types of received data. Common ABF approaches can use second order statistics of the received data to compute phase and amplitude weights, such as to minimize beamsum energy, while constraining the response in the look-direction. For example, in passive SONAR, numerous looks at the environment can provide estimation of second order statistics. However, such techniques can have limitations if used for transmit/receive systems (in contrast to passive systems). ABF can incorporate diagonal loading such as to obtain a stable covariance matrix, although such techniques may achieve little improvement in image quality over convention beamforming (CBF). Other ABF approaches can include reduced rank beamformers or oblique projections, but such techniques can still be susceptible to model inaccuracies. In other approaches, received echo data statistics are not relied upon; such approaches can be used for pulse-echo imaging, such approaches including a generalized eigenvalue approach, a Bayesian approach, a maximum likelihood estimation approach, a data-adaptive regularization approach, or a minimum worst-case gain approach, among others.

The present inventors have recognized, among other things, that ultrasound imaging's characteristics can make successful application of existing ABF techniques problematic. Generally, in ultrasound applications, only limited statistics are available to form a covariance matrix. Moreover, on-axis and off-axis signals can be strongly correlated. Also, ultrasound is generally performed with broadband signals in the near-field, whereas most ABF techniques generally use narrowband signals in the far-field. Thus, ultrasound image reconstruction can present numerous challenges that are not apparent in either RADAR or SONAR. Specifically, broadband interrogation, highly correlated clutter and target signals, near-field operation, and limited statistical information make ultrasound a particularly challenging problem. In an approach, a Time-domain, Optimized, Near-field Estimator (TONE) can be used to determine weights of one or more candidate targets included in a region of interest, such as according to one more techniques or systems disclosed in U.S. patent application Ser. No. 11/992,368, incorporated above by reference in its entirety, or similarly described in the examples of FIGS. 3-4 below.

However, use of TONE can be computationally intensive as compared to CBF or other conventional image reconstruction (CIR) techniques (e.g., including delay-and-sum beamforming), such as when a system including only a single processor is used for image reconstruction. Thus, the present inventors have recognized that one or more systems, methods, or computer program products can include a so-called "quick Time-domain, Optimized, Near-field Estimator (qTONE)." Such a qTONE estimator can include determining weights of one or more candidate targets using a singular value decomposition technique, such as to solve a constrained least-squares problem, such as minimizing an argument to a function including a probability distribution modeling the weights of the candidate targets in a region of interest.

Also, the present inventors have recognized that a system or method, such as including TONE or qTONE, can produce undesired image artifacts, such as when a model matrix including crisply-defined candidate targets is used. Thus, the present inventors have recognized that one or more systems, methods, or computer program products can include a so-called "diffuse, Time-domain, Optimized, Near-field Estimator (dTONE)," such as using a system model matrix (e.g., an array manifold matrix), including one or more diffusely-modeled candidate targets.

One or more techniques, such as discussed in the examples below can be used to perform image reconstruction or target localization (e.g., emitter localization), such as including models that can assume targets that scatter uniformly in all directions (e.g., compressibility scatterers) or that scatter preferentially in the direction of the incident wave with a cosine dependence (e.g. density scatterers).

Hardware Platform

FIG. 1 illustrates generally an example of portions of a system 100 and portions of an environment in which the system 100 can be used. In an example, the system 100 can include a first processor circuit 122, a memory circuit 124, a display 128, a storage unit 130, one or more transducers 110, an analog front-end 106 coupled to the one or transducers 110 (e.g., a transducer or an array of transducers), such as via a bus 112, one or more analog-to-digital (A/D) converters 108, and a digital logic circuit 114 such as including one or more buffers. In FIG. 1, one or more of the memory circuit 124, the first processor circuit 122, or one or more additional processor circuits such as a second processor circuit 118 can be included in a computer system 126. Such as computer system 126 can include a hand-held or tablet computer, a desktop computer, a laptop computer, a computer server, or a combination of one or more general purpose or special purpose computers, such as configured to receive an echo data set from a transducer block 120, such as via a wired or wireless communication link 116A.

In an example, a region of interest 132 can include one or more actual targets such as a first target 102. The region of interest 132 can be excited (e.g., insonified, etc.) such as using energy provided by the one or more transducers 110, such as under the control of the first processor circuit 122. For example, a transmitted ultrasonic energy pulse 104A can propagate through the region of interest 132, and a portion of the transmitted energy pulse 104A can be scattered or reflected by one or more targets, such as the first target 102, to provide an echo 104B. The one or more transducers 110 can be configured to receive a portion of the echo 104B. The analog front end circuit 106 can be configured for processing the resulting transduced echo signal, such as conditioning, delaying, filtering, or otherwise processing the received echo 104B. Signal processing can further include converting the received energy from an analog signal representation into a digital representation, such as using one or more of the analog-to-digital converters 108. In an array example, one or more of the bus 112, the A/D converters 108, or the digital logic circuit 114 can include a signal channel corresponding to a respective transducer included in an array of transducers 110. For example, a transducer in the array of transducers 110 can be coupled to a respective portion of the analog front end 106, including a respective analog-to-digital converter, or buffered by a respective digital buffer. In an array example, one or more portions of the analog front end 106, the one or more analog-to-digital converters 108, or the digital logic circuit can be commonly-shared between two or more transducers, such as to simplify the construction of an ultrasonic transducer assembly 120, such as multiplexed over time (e.g., within a single transmission or across multiple transmissions).

In an example, the storage unit 130 can be included as a portion of a general or special purpose computer, such as the computer system 126. For example, an echo data set can be received from the ultrasonic transducer assembly 120, and stored on the storage unit 130, such as transferred to the storage unit 130 via a wired or wireless communication link 116C. In an example, the echo data set can be processed, such as to reconstruct an image including a representation of the location of the target 102. Such processing need not occur using the same computer system 126 as can be used to control the transducer assembly 120. For example, a physically-separate computer, processor, or remote "computer farm" can be used to perform a numerical estimation or image reconstruction, such as to provide an estimate to be shown on a display 128 coupled to the computer system 126, the display communicated via a wired or wireless communication link 116B.

One or more techniques such as included in the examples of FIGS. 2-9 can be machine-implemented or computer implemented, such as performed by the system 100 corresponding to instructions stored in one or more of the memory circuit 124 or the storage unit 130, among others. In an example, one or more of the memory circuit 124 or the storage unit 130 can include a processor-readable medium, such as comprising instructions that when performed by the first or second processors 122, 118, cause the processors or system to perform one or more of the techniques included in the examples of FIGS. 2-9.

In an example, the first or second processors 122, 118, can include one or more application-specific integrated circuits (ASICs), such as one or more graphical processing units (GPUs). For example, a GPU can be highly efficient for image processing or dense linear algebra due to parallelism inherent in the GPU design, or due to regular data access patterns. In an illustrative example, a portion of the system 100, such as including the first or second processors 122, 118 (or one or more additional processors), can include a TESLA high-performance computing module, such as provided by nVidia Corporation, Santa Clara, Calif. It is believed that such a TESLA computing module can provide a 10-50× speedup (or more, depending in part on a number of processor cores), as compared to a single-processor CISC architecture, using basic data layout techniques in a variety of applications. It is believed that such a TESLA computing module can provide up to 200× speedups on iterative solvers with more aggressive algorithmic restructuring to increase parallelism. Further speedups are believed to be possible if matrices are reused, such as in relation to the examples of FIGS. 2-9, (e.g., where the largest matrix operand can remain resident across frames). It is believed that a C-like programming language—CUDA—for GPUs in such TESLA modules can greatly simplify programming. In another example, the first or second processors can include one or more field-programmable gate arrays, such as including a gate or register configuration selected for implementation of a portion of one or more techniques shown in the examples of FIGS. 2-9.

In an example, the one or more transducers 110 can be configured to insonify the region of interest 132 using ultrasonic energy, and the region of interest can include a tissue region (e.g., a breast region, a testicular region, or one or more other locations). In such an illustrative tissue imaging example, the target 102 can represent a cyst, or other inhomogeneity in the region of interest 132. In such an illustrative tissue imaging example, reflected energy can include an ultrasonic echo 104B that can be digitized and converted to an echo data set provided to the computer system 126. For example, the computer system 126 can then provide an image, such as using the display 128, using an estimate of the target 102 location, such as using one or more techniques shown in the examples of FIGS. 2-9.

Image Reconstruction Such as Using an Echo Data Set and a System Model Matrix

Figure 2:
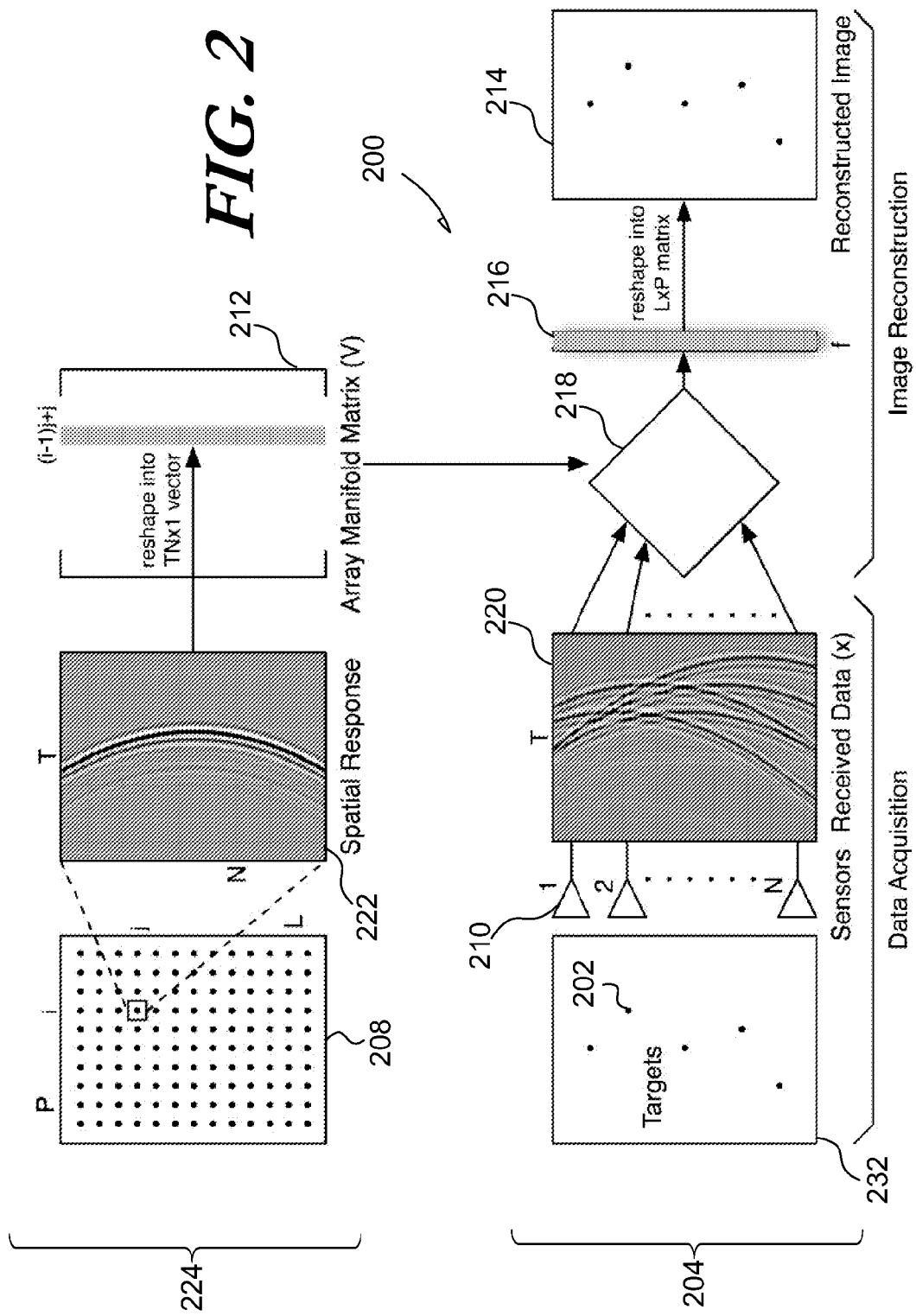
FIG. 2 illustrates generally an example of a technique for reconstructing an image, such as including one or more actual targets.

FIG. 2 illustrates generally an example 200 of a technique for reconstructing an image 214, such as including one or more actual targets such as a target 202 included in a region of interest (ROI) 232 (e.g., in a plane or volume of space to be imaged or otherwise analyzed). The example of FIG. 2 can be used, such as by the system 100 of FIG. 1, to provide an image, such as estimating a location of the target 202 included in the ROI 232. In FIG. 2, a system model can be selected or generated such as shown in a portion 224 of the example 200. For example, an array 208 of candidate targets (e.g., one or more hypothetical targets) can be modeled and transformed into a system model matrix 212 (e.g., an "array manifold matrix"). In a portion 204 of the example 200, the one or more actual targets can provide echo energy to one or more transducers such as a transducer 210. The received echo energy can be digitized and transformed into a received data array, such as an echo data set 220. At 218, a weight of any one or more of the candidate targets from the array 208 can be determined, using the echo data set 220 and the system model matrix 212, to provide a vector 216 including information estimating the actual target configuration. In an example, at 214, the vector 216 can be transformed into an array (e.g., an array of brightnesses or magnitudes, or a complex array that can include both magnitude and phase information), such as to reconstruct an image 214 representing an estimate of the configuration (e.g., location) of one or more actual targets, such as the target 202.

In an example, the ROI 232 can be first subdivided into a collection of hypothetical (e.g., candidate targets) at specified (e.g., arbitrary) positions, to provide the array 208. For example, the nature of a candidate target can depend on the modality in which the image reconstruction is being applied; for example, in medical ultrasound, the candidate targets can include point scatterers, but the modeled targets need not be restricted to point scatterers. For example, a modeled candidate target can include an angular scattering profile, or a frequency-dependent scattering behavior, among others.

While any sampling can be specified, the example of FIG. 2 a uniform rectangular grid for simplicity and ease of display. Generally, a finer grid sampling can yield a finer resolution for a reconstructed image 214 estimate, but at a higher computational cost.

In an example, for a candidate target in the ROI 232, a signal received by the sensor array from a target at that specific point can be modeled to provide a predicted spatial response 222, such as for each candidate target. The spatial response 222 of the candidate target can include a matrix of dimensions T×N, where T can represent the number of samples in a temporal dimension and N can represent the number of elements in the array 208, regardless of the array 208 geometry. After the spatial responses for all of the candidate targets have been determined, such as experimentally, or via theory or simulation, they can be reshaped, such as into column vectors and concatenated to form an array manifold matrix (e.g., a system model 212), V. The array manifold matrix V can have dimensions NT×LP, where L and P can represent the numbers of candidate targets in two spatial dimensions. In an example, some modalities need not use sampling in the temporal dimension (T=1), and some can include spatial sampling of the hypothetical targets in more than the two dimensions, such as described by L and P.

An observation "model," such as corresponding to a received echo data set, can then be represented by x=Vf, where $x=[x_1 x_2 \ldots x_{NT}]^T$ can represent the data received by an "N" element array including the transducer 210. The vector representing the estimated target vector, f, can be re-shaped into a matrix representation of the reconstructed image 214, whose elements can include the amplitudes (e.g., "weights") of the candidate targets located in the ROI 232. In an example, x is the NT×1 vector obtained by concatenating the channel data (e.g., the echo data set 220) into a vector representation.

The examples of FIGS. 2-9 can treat image formation (e.g., reconstruction of an image of one or more actual targets in a region of interest) as an underdetermined problem, such as with many more targets in the field than data points acquired in an echo data set. In one approach, such as included in the examples of FIGS. 3-4, a Maximum A Posteriori (MAP) estimator can be used to find a minimum energy candidate target configuration such as yielding the received echo pattern. Such an approach can begin using a linear model for echo formation, which can be represented by x=Mf, where x can represent the received echo data set (e.g., concatenated into a vector), such as from all array elements reshaped into a vector, and f can represent a vector such as including a weight of any one or more candidate targets (e.g., hypothetical targets), such targets represented by a system model matrix, M, (e.g., an array manifold matrix). Such a model (as in the example of FIG. 2) can assume that echo data set can represent a linear superposition of echoes from individual scatterers (e.g., one or more actual targets in the ROI).

The array manifold matrix, M, can model a shift-variant system, or can allow for non-linear propagation of the transmit beam. The array manifold, M, can incorporate the predicted echo signals, such as received from a finite set of scatterers at discrete locations. In an example, the array manifold matrix can be specified (e.g., selected from amongst many possible matrices or generated), such as to fit an expected target configuration (e.g., actual target configuration), depending on the mode (e.g., ultrasound) or application (e.g., tissue composition or location, among others) of the image reconstruction technique.

Time-Domain, Optimized, Near-Field Estimator (TONE) Examples

Figure 3:
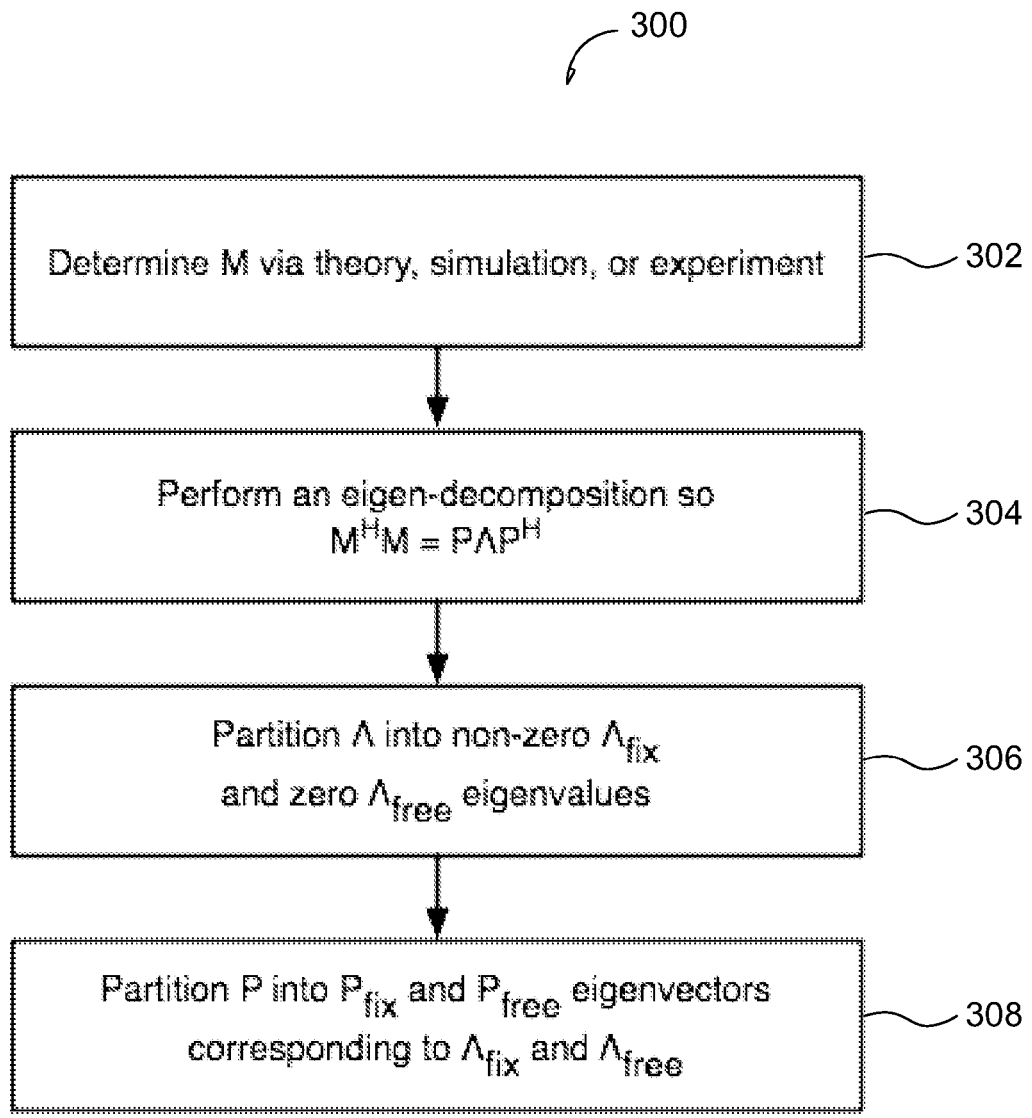
FIG. 3 illustrates generally an example of a technique including manipulating a system model matrix, such as included as a portion of the technique of FIG. 2.

FIG. 3 illustrates generally an example 300 of a technique including manipulating a system model matrix "M" (such as the array manifold matrix "V" of the example of FIG. 2), such as can be performed using one or more portions of the system of FIG. 1. At 302, the system model matrix M can be determined such as via theoretically modeling, simulating, or experimentally measuring a spatial response of a transducer system in the presence of one or more candidate targets (e.g., as in the example FIG. 2). At 304, an eigendecomposition can be performed on the system model matrix M.

At 306, the resulting eigenvalue matrix can be partitioned into zero-valued eigenvalues and non-zero eigenvalues. The zero-valued eigenvalues need not be identically zero. For example, such as including a system as in FIG. 1 using one or more techniques of FIGS. 2-3, a partitioning of eigenvalues can be based on "epsilon" (e.g., a machine working precision), rather than zero. Similarly, at 308, an eigenvector matrix, P, determined from the model matrix, M, can be partitioned into eigenvectors (e.g., $P_{free}$) corresponding to zero-valued eigenvalues, and eigenvectors ($P_{fix}$) corresponding to non-zero-valued eigenvalues. In an example, the eigenvalues can be partitioned using a specified level or a margin above epsilon, such as to stabilize or smooth image formation.

Figure 4:
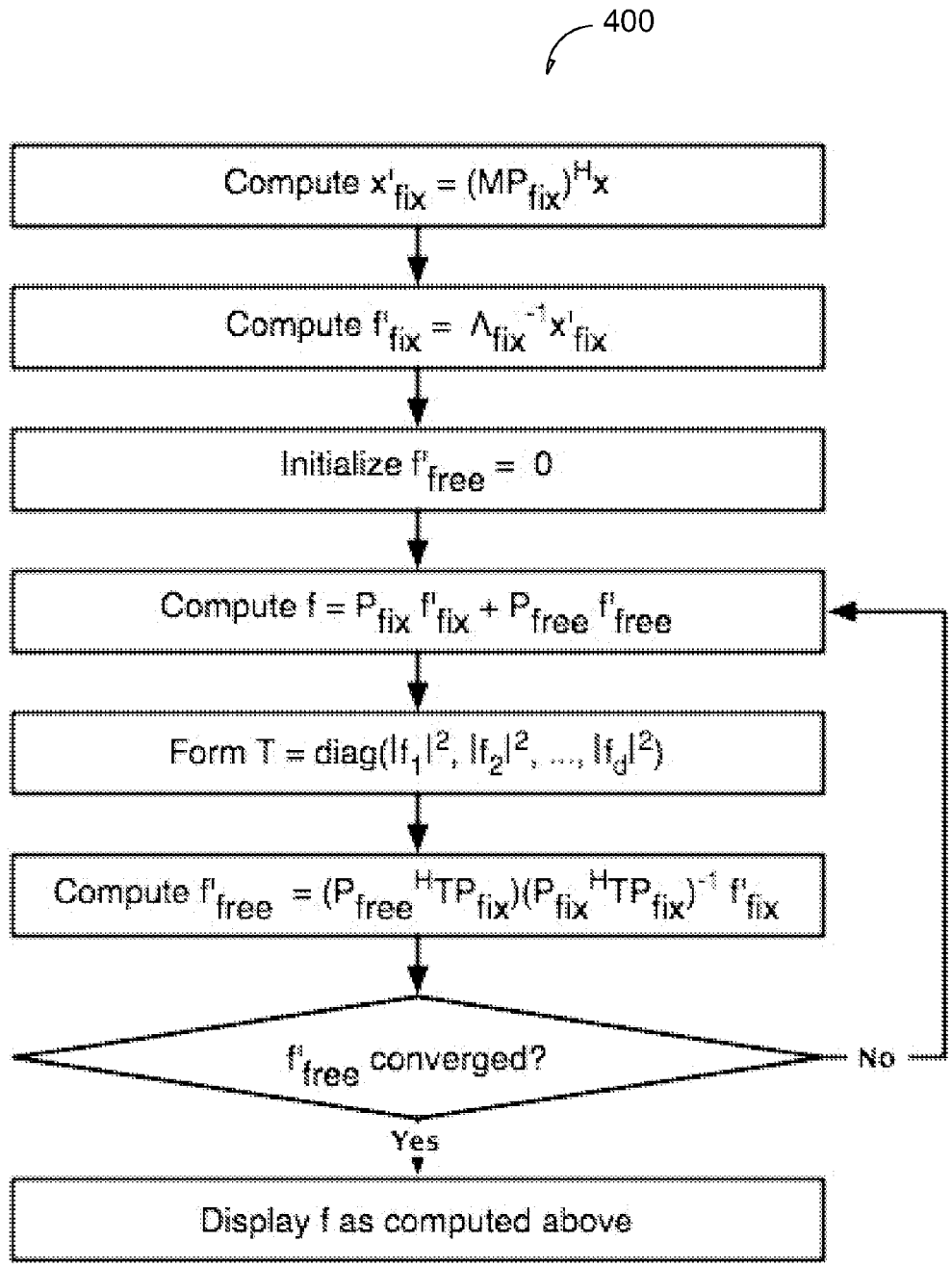
FIG. 4 illustrates generally an example of a technique that can be iterative, such as for determining weights of any one or more candidate targets, such as included as a portion of the example of FIG. 2, or using information provided by the technique of FIG. 3.

FIG. 4 illustrates generally an example 400 of a technique that can be iterative, such as for determining weights of any one or more candidate targets, such as included as a portion of the example of FIG. 2, or using information provided by the technique of FIG. 3. A vector, f, can represent an estimate of an actual target configuration, as shown in the examples of FIGS. 1-2, where the weights of any one or more candidate targets can be estimated using the iterative approach of FIG. 4, such as using one or more processors as shown in the system of FIG. 1. The resulting weights can be used to provide an image, such as including brighter areas at the discrete target locations defined in the system model matrix (e.g., "V" or "M".) In an illustrative example of an ultrasonic application, such an iterative approach can converge in three iterations.

Diffuse Time Domain Optimized Near-Field Estimator (dTONE) Examples

Figure 5:
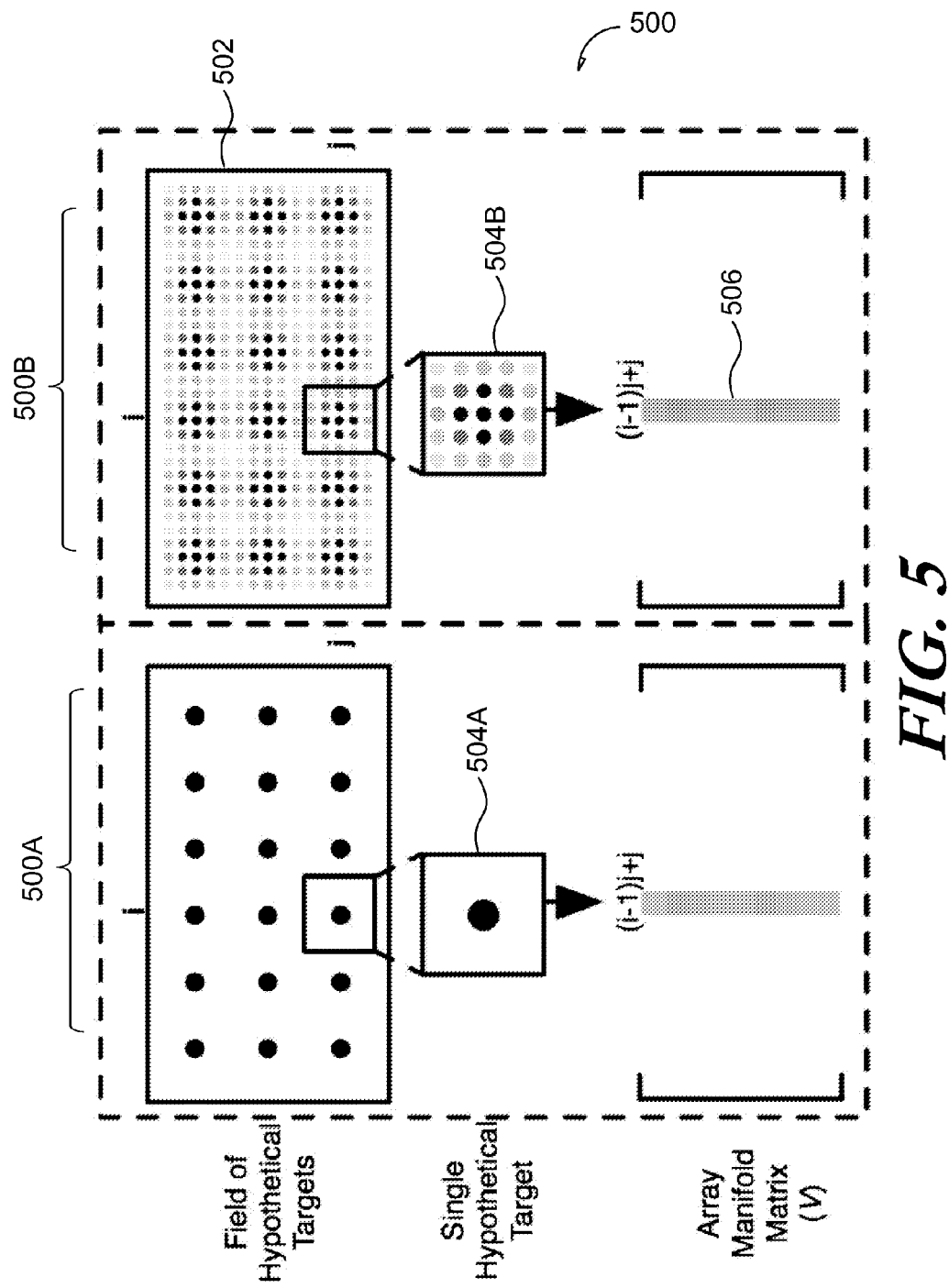
FIG. 5 illustrates generally an example of modeling a region of interest using a crisply-modeled candidate target, or using a diffusely-modeled candidate target.

FIG. 5 illustrates generally an example of modeling a region of interest 502 that can include a crisply-modeled candidate target 504A, or a diffusely-modeled candidate target 504B, such as included in a column 506 of a system model matrix (e.g., an array manifold matrix).

In the examples of FIGS. 2-3, and below in the examples of FIGS. 6-7, a reconstructed image representing an estimate of one or more target locations using one or more crisply-modeled targets can be highly pixellated. Such pixellation can be troublesome in distributed scattering environments. (e.g., such as in an ultrasound application). For example, in an application involving tumor identification (e.g., wherein one or more actual targets includes a lesion), such pixellation can reduce lesion detectability, making image interpretation more difficult. Also, even relatively accurately-estimated target locations can be accompanied by local clutter in a reconstructed image based on the estimate. It is believed that such pixellation or local clutter (e.g., ghosting, etc.) can result from locating candidate (e.g., hypothetical) targets on a fixed grid, while actual targets need not lie at these locations. For example, since ultrasound data can be coherent and therefore subject to constructive or destructive interference, the estimated candidate target weights that might best model data from an actual (e.g., real) target may not lie adjacent to the actual target location.

In an illustrative example, an individual crisp target, such as a candidate target 504A, can be replaced with a "cloud" including 5×5 targets weighted such as using separable cubic b-splines, or some other smoothing function. Such a candidate diffuse scatterer can include a weighted sum of sources in a finite region rather that a single discrete scatterer. In such a b-spline example, a compact region of support is provided and a smoother target space can be realized, as shown in the region 502. In the example of the diffuse target 504B, generation of M or V can take longer than generating or modeling a system model including crisply-defined targets. However, the array manifold matrix need not increase in size, as the number of candidate targets can remains constant. Thus, an image reconstruction using diffuse candidate targets need not take additional time or memory as compared estimating candidate target weights using crisp targets. Such diffusely-modeled candidate targets can be used for image reconstruction, such as using the system of FIG. 1, and combined with one or more techniques such as included in FIGS. 3-4 or FIGS. 6-7 (e.g., substituting a diffuse target model for a crisp target model). In an example, similar b-splines such as used to generate or model target distribution can also be used for image display.

Quick Time-Domain Optimized Near-Field Estimator (qTONE) Examples

The present inventors have also recognized that the examples of FIGS. 3-4 can significantly improve contrast and spatial resolution as compared to conventional beamforming (CBF), such as when applied to medical ultrasound, but such techniques can still have a significant computational cost. A marginal probability density function can be used to represent a distribution of candidate target weights, such as to be estimated using a system model as shown in the example of FIG. 2. For example, a zero-mean Gaussian distribution can be used to model a distribution of candidate target weights:

$$p(f) = \frac{1}{\pi^d |C_f|} \exp\{-f^H C_f^{-1} f\} \qquad \text{(EQN. 6.1)}$$

where d can represent a number of candidate targets, and f can represent a vector of candidate target weights (e.g., target "brightnesses"). In EQN. 6.1, $C_f$ can represent a covariance matrix of the candidate target weights. In the examples of FIGS. 3-4, a maximum a posteriori (MAP) estimator can use a log-likelihood function of the distribution of EQN 6.1 to estimate the candidate target weights. But, such a log-likelihood function can be responsible for the computationally intensive matrix inversion, $(P_{fix}{}^H T P_{fix})^{-1}$, such as used during an iteration of the technique of FIGS. 3-4, and shown in FIG. 4.

In contrast, rather than maximizing the log-likelihood function, the present inventors have also recognized that the value of the exponential term of the Gaussian distribution can instead be maximized, such as by minimizing an argument to the exponential term. Such a minimization can present a different optimization problem that can be represented as:

$$\min f^H C_f^{-1} f \text{ s.t. } x = Mf \qquad \text{(EQN. 6.2)}$$

The new problem of EQN. 6.2 can be a constrained least-squares problem, and can have a solution represented by:

$$\hat{f} = C_f M^H (M C_f M^H)^{-1} x \qquad \text{(EQN 6.3)}$$

In an example, the term, $MC_f M^H$, can be ill-conditioned, but the problem can be regularized, such as represented by a modification to EQN. 6.3:

$$\hat{f} = C_f M^H (M C_f M^H + \sigma I)^{-1} x \quad \text{(EQN. 6.4)}$$

Although the above technique can be more computationally efficient than the MAP estimation technique of the examples of FIGS. 3-4, the present inventors have also recognized that there are additional improvements that can be applied, such as to further reduce computational burden. For example, a system model matrix (e.g., an array manifold matrix such as shown in FIGS. 2-5, including a matrix M or V), is generally not full rank in realistic problems. Thus, a range of techniques can be used to express the system model matrix (e.g., the array manifold matrix) more efficiently.

Figure 6:
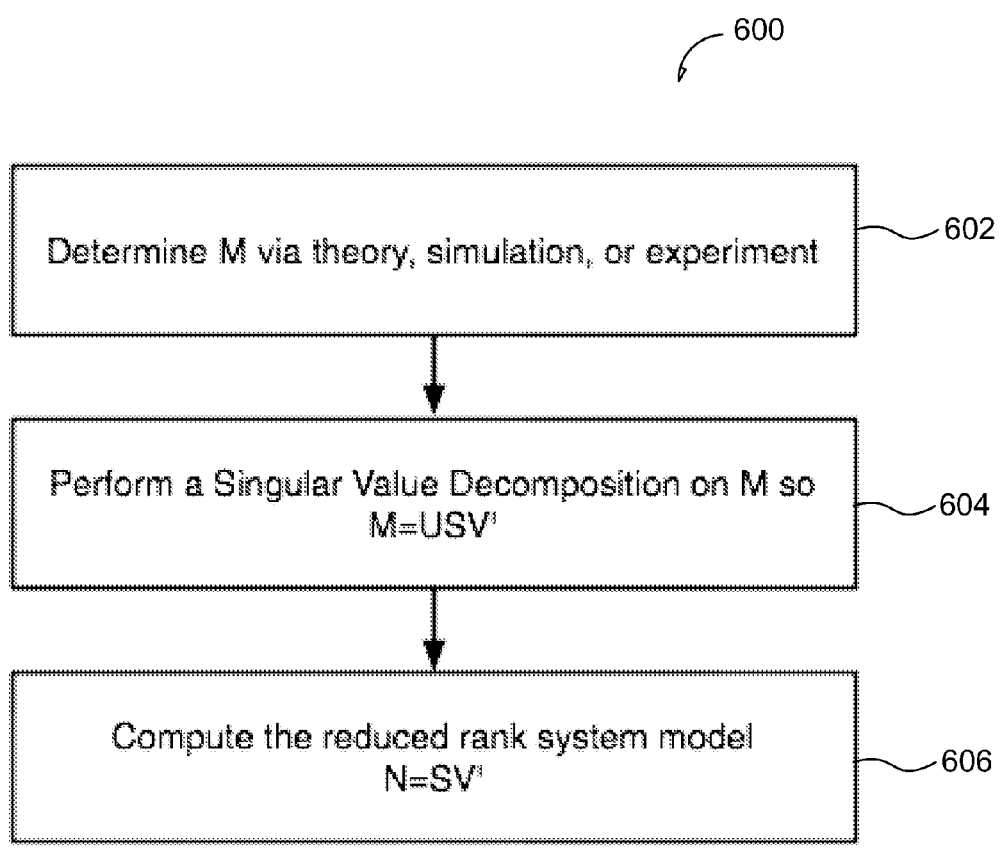
FIG. 6 illustrates generally an example of a technique including performing a singular value decomposition on an array manifold matrix, the array manifold matrix modeling a region of interest and including information corresponding to one or more candidate targets included in the region of interest.

FIG. 6 illustrates generally an example 600 of a technique including performing a singular value decomposition on an array manifold matrix, the array manifold matrix modeling a region of interest and including information corresponding to one or more candidate targets included in the region of interest. At 602, a system model matrix, M, can be selected or generated, such as discussed above with respect to the examples of FIGS. 2-5, including one or more crisply-modeled or diffusely-modeled candidate targets. At 604, Singular Value Decomposition (SVD) can be performed such as to develop a more "compact" model representation, such as represented by:

$$M = U S V^H \quad \text{(EQN 6.5)}$$

An echo data set can be represented by x, and a corresponding relationship between the "compact" array manifold representation, the echo data set, and an vector f representing an estimate of the weights of the candidate targets can be represented by:

$$x = U S V^H f \quad \text{(EQN. 6.6)}$$

In an example, both sides of EQN 6.6 can be multiplied by the inverse of U (e.g., using the matrix U provided by the singular value decomposition in EQN. 6.5) resulting in a transformed (e.g., projected) system model that can be represented by:

$$y = N f \quad \text{(EQN 6.7)}$$

such as where $y = U^{-1} x$ and $N = S V^H$.

In an example, the application of SVD will ensure that the transformed array manifold matrix, N, has at least a partially empty structure. For example, the lower the original rank of M, the smaller the non-zero extent of N. Since N can have a large zero extent, it can be expressed by:

$$N = \begin{bmatrix} Q \\ 0 \end{bmatrix} \quad \text{(EQN. 6.8)}$$

Such an SVD formalism can be used to re-define the target estimation of equation 6.3, such as represented by:

$$f = C_f [Q^H \ 0] \left( \begin{bmatrix} Q \\ 0 \end{bmatrix} C_f [Q^H \ 0] + \sigma I \right)^{-1} \quad \text{(EQN. 6.9)}$$
$$y = [C_f Q^H (Q C_f Q^H)^{-1} \ 0] y$$

One or more of the techniques of FIGS. 5-6 can be performed, such as using a system 100 as shown in FIG. 1, either at run-time (e.g., during an estimation), or such as determining one or more transformed system model matrices in advance (e.g., determining one or more reduced-rank array manifold matrices in advance of estimation). For example, an SVD can be performed, such as to provide the transformed model matrix N at a different time than during estimation of the weights of the candidate targets as shown in the example of FIG. 7.

Figure 7:
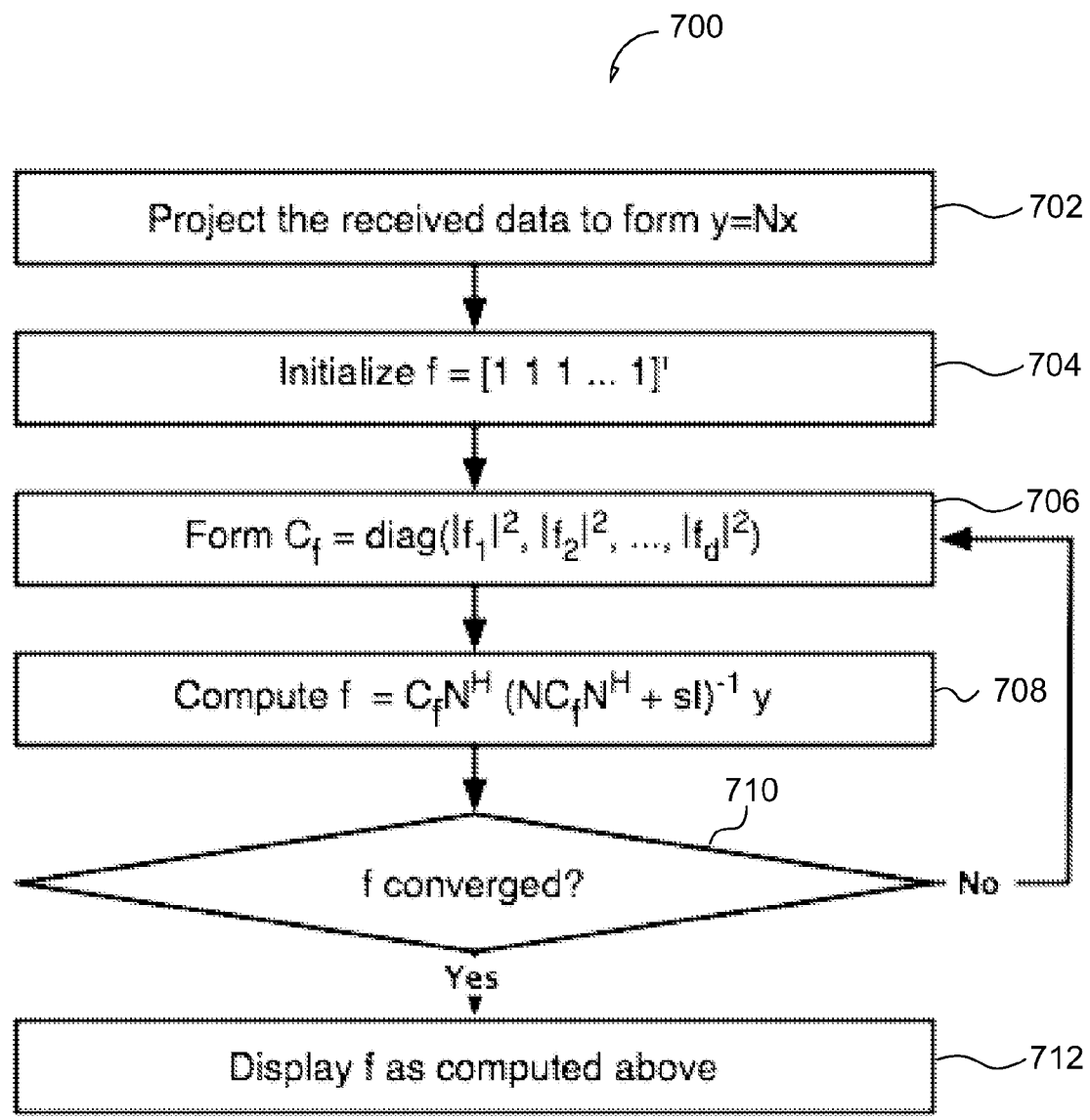
FIG. 7 illustrates generally an example of a technique that can be iterative, such as for determining weights of any one or more candidate targets, such as included as a portion of the example of FIG. 2, or using information provided by the technique of FIG. 6.

FIG. 7 illustrates generally an example 700 of a technique that can be iterative, such as for determining weights of any one or more candidate targets, such as included as a portion of the example of FIG. 2, or using information provided by the technique of FIG. 6, such as using an iterative candidate target estimation technique, such as represented by EQN 6.9. At 702, a received echo data set (such as corresponding to energy received using a transducer as shown in FIGS. 1-2) can be represented by x. The received echo data set x can be projected onto a different space using a transformation matrix, N, such as determined using singular value decomposition (SVD) as shown in the example of FIG. 6. At 704, an initial guess can be made, such as populating an estimate of the weights of candidate targets included in the array manifold matrix with specified values (e.g., all "1s," or some other seed). At 706, a covariance matrix can be determined, such as represented by:

$$\hat{C}_f = \text{diag}(|f_1|^2, |f_1|^2, \ldots, |f_d|^2) \quad \text{(EQN. 7.1)}$$

At 708, a new estimate of a vector representing the weights of the candidate targets can be determined, such as using compact system model, and can be represented by:

$$\hat{f} = \hat{C}_f N^H (N \hat{C}_f N^H + s I)^{-1} y \quad \text{(EQN. 7.2)}$$

In an example, EQN. 7.2 can but need not include a regularization term, sI, (e.g., s can be zero). At 710, a result of the present iteration, $\hat{f}$, can be compared with a previously-estimated vector of candidate target weights. If $\hat{f}$ has not converged, the technique of FIG. 7 can form a new covariance matrix at 706, and repeat the determination at 708, such as represented by EQN. 7.2, but using the updated covariance $\hat{C}_f$. At 712, if $\hat{f}$ has converged (e.g., a difference between a presently-determined estimate $\hat{f}$ and the previous estimate deviate from one another less than a specified amount), then the estimate $\hat{f}$ can be displayed or otherwise communicated for further presentation, storage, or processing, such as shown in the system 100 of FIG. 1.

Spatial and Temporal Tiling, Such as to Reduce Computational Burden

In the examples of FIGS. 2-7, the candidate targets (e.g., one or more hypothetical scatterers) that can produce a detectable signal in the received data should all be appropriately modeled. Otherwise, a resulting estimate of target locations can include cloud-like artifacts, such as significantly decreasing the contrast of the reconstructed images. Thus, direct parallelization of determining the weights of the one or more candidate targets (e.g., using multiple processors such as included in the example of FIG. 1) can cause image quality to suffer.

The present inventors have also recognized that in order to successfully partition the techniques of FIGS. 2-6, one or more scatterers not in the reconstructed image but still insonified by the transmit pulse can still be appropriately modeled in a reduced form. For example, a rank reduction technique can allow for one or more such "outside scatterers" to be efficiently modeled such that one or more of the techniques of FIGS. 2-7 can be parallelized or otherwise partitioned to reduce computation time with minimal loss in image quality. Such partitioning can be applied either spatially or temporally.

In an example, if not all candidate targets (e.g., hypothetical sources) need to be displayed in a reconstructed image, the dimensionality of array manifold matrix and corresponding system model can be reduced to its principal components. For example, the set of hypothetical source locations (e.g., candidate targets) can be divided into two non-overlapping subsets, such as one for display (e.g., one or more "inside" scatterers) and one to prevent image degradation such as from bright un-modeled sources (e.g., one or more "outside" scatterers). In an example, principal component analysis can be applied to the outside scatterers to find a reduced rank set of orthogonal vectors spanning almost the entire space spanned by the full set of outside scatterers. Such a reduced set of outside scatterers can then concatenated with a full set of inside scatterers, such as to form a hybrid model matrix that can be used with the techniques of FIGS. 2-7 (e.g., a modified array manifold matrix). Generally, the rank-reduced set of outside scatterers can contain most of the information corresponding to the full set, but would not have the same spatial localization. As a result, the subset of the reconstruction from the rank reduced set of outside scatterers could not be itself used to form an image, but can still can still help prevent "bright" outside scatterers from degrading the reconstruction of inside scatterers.

Figure 8:
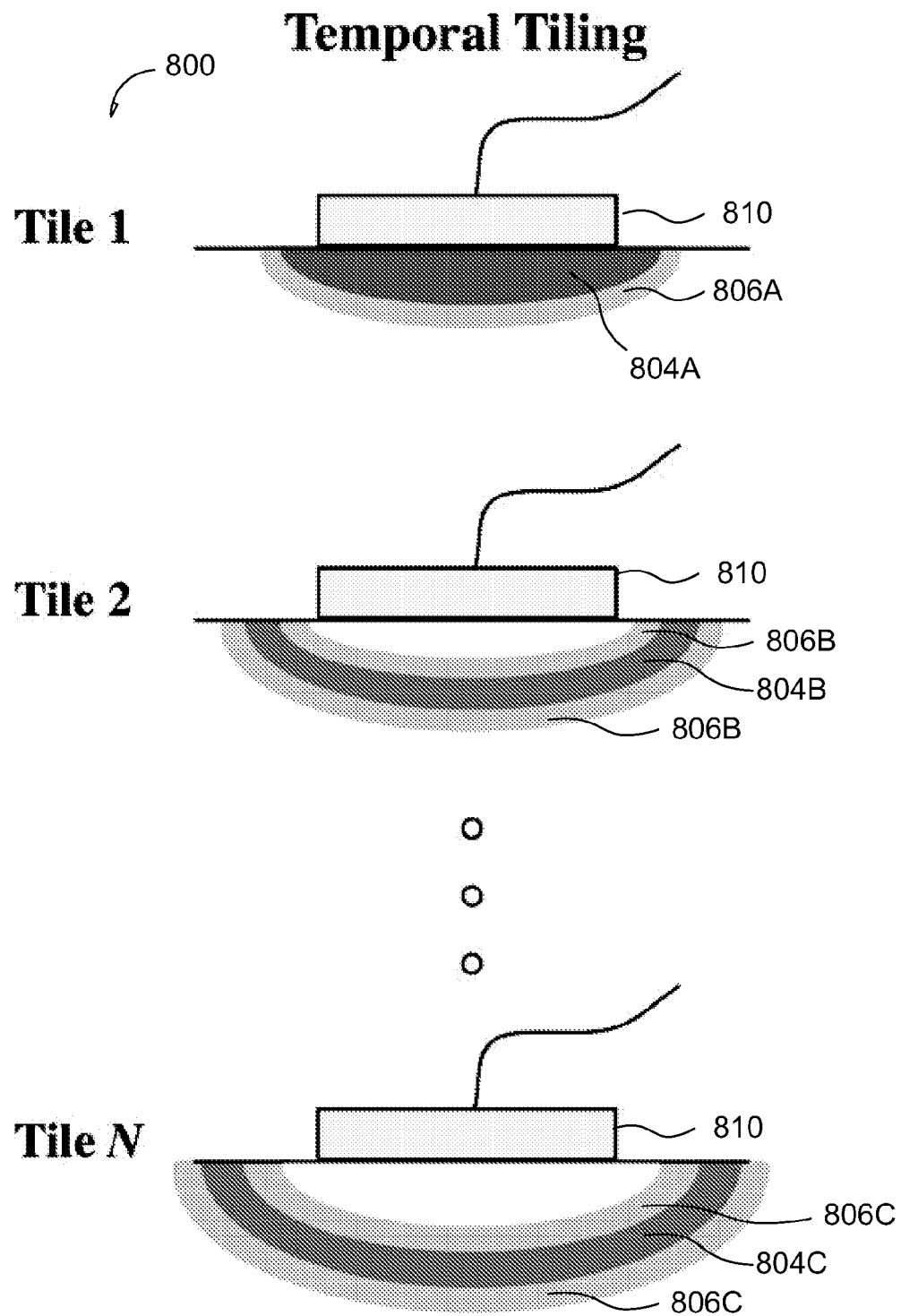
FIG. 8 illustrates generally an example of subdividing a region of interest temporally, such as to reduce a computational burden in determining weights of any one or more candidate targets included in the region of interest.

FIG. 8 illustrates generally an example 800 of subdividing a region of interest temporally, such as to reduce a computational burden in determining weights of any one or more candidate targets included in the region of interest, such as using an echo data set corresponding to energy received by a transducer 810. The technique of FIGS. 8-9 can be used in combination with one or more of the examples of FIGS. 1-7, such as to partition a determination or otherwise enhance computational efficiency in determining one or more weights of one or more candidate targets.

In an ultrasound example, because ultrasound imaging is a pulse-echo modality, echoes arriving within a specified time window can originate from a specific set (e.g., a locus) of locations. For example, for an ideal point transducer emitting a temporal delta function, the echoes arriving in the first 10 µs originate from within a radius of about 7.7 mm, assuming a speed of sound of about 1540 m/s. In an illustrative example, real ultrasound systems (such as shown in the example of FIG. 1), can use arrays of transducer elements and emit pulses of finite temporal duration. In such systems, a specified temporal window of echo data (e.g., a portion of an echo data set) can be partitioned into at least two segments (e.g., a first interval and a second interval). A first segment, herein called the "complete set," 804A-C can originate from scatterer locations for which the entire echo is captured by every element in the array (e.g., without spatial truncation). A second segment, herein called the "partial" set 806A-C, can originate from scatterer locations for which only a partial set of echo data is acquired, either in truncated in time or truncated spatially along the array of transducer 810 elements. The complete set 804A-C and the partial set 806A-C can overlap in time, but not in space. Temporal "tiling" can exhibit less image degradation than spatial tiling for equal computational cost reductions, especially as the number of tiles are increased, since each window of channel-time data (e.g., each "tile") used can only arise from a limited set hypothetical scatterers (e.g., within the locus determined in part by propagation velocity).

In an example, one or more of the candidate target determination techniques of FIGS. 2-7 can be performed on partially overlapping temporal windows of echo data (e.g., tiles 1, 2 . . . N). For each temporal window a region of the scatterer configuration is estimated using the portion of the system model that contributes signals to that particular temporal window (e.g., a particular tile). However, only the portion of the region of interest for which the complete set 804A-C of echo data was acquired is reliable. Thus, in an example, the complete set 804A-C is used in full to update the final image reconstruction (e.g., a composite determination of weights) and the partial set 806A-C is rank reduced and used to improve the robustness of the reconstruction for a particular full set 804A-C.

Figure 9:
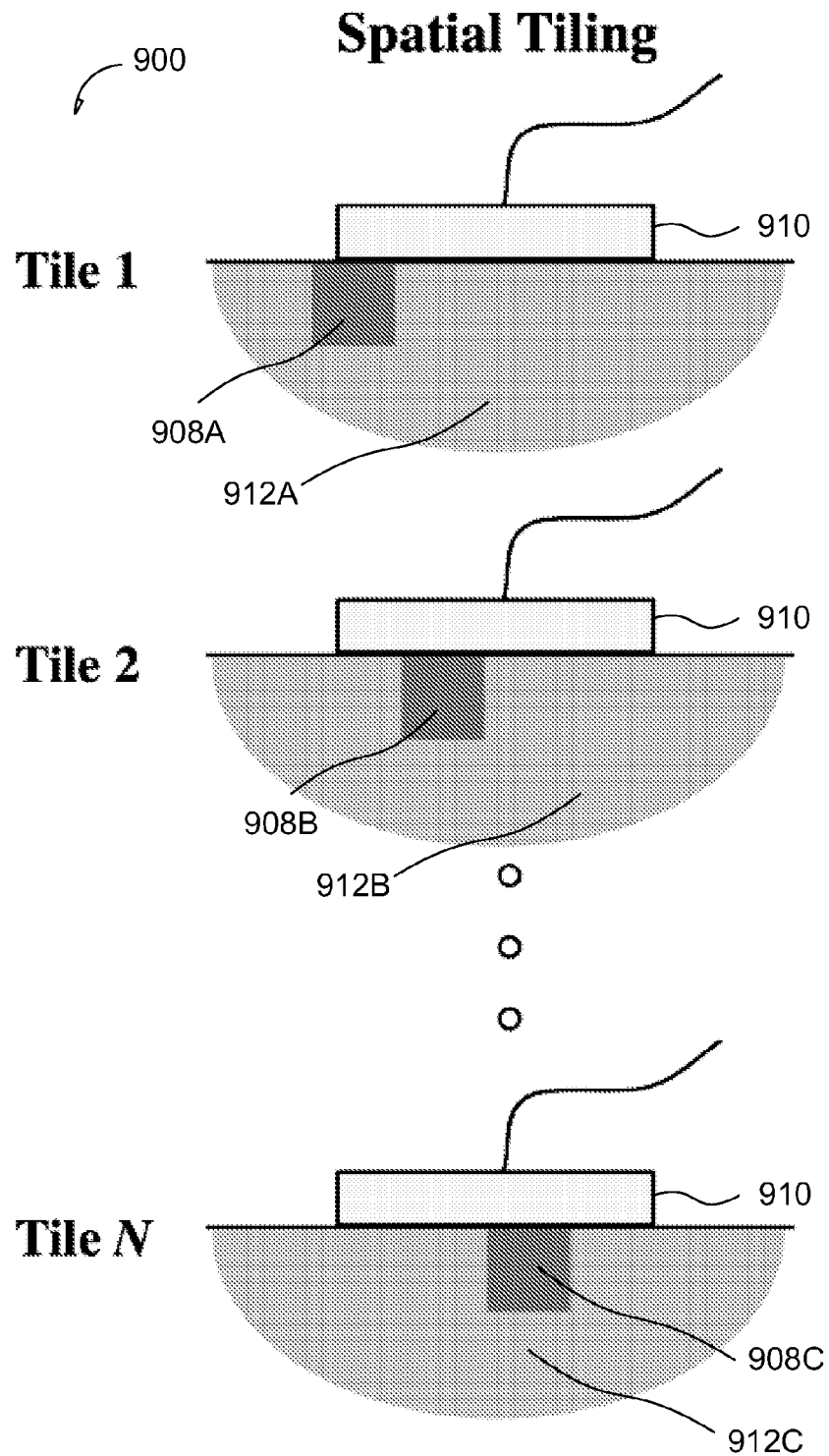
FIG. 9 illustrates generally an example of subdividing a region of interest spatially, such as to provide a reduced-rank system model matrix for a portion of the subdivided region of interest.

FIG. 9 illustrates generally an example 900 of subdividing a region of interest spatially, such as to provide a reduced-rank system model matrix for a portion of the subdivided region of interest (ROI). As in the example of FIG. 8, the spatial subdivision in FIG. 9 can be used with one or more of candidate target determination techniques discussed above in the examples of FIGS. 2-8.

In an example, a simple way to divide the region of interest can be to spatially partition (e.g., subdivide) a set of hypothetical scatterers (e.g., candidate targets) into equally-sized tiles. Although FIG. 9 depicts these tiles as squares, they can each be of any specified size or shape as long tiles together cover the entire ROI. Similarly to the temporal partitioning example of FIG. 8, the responses of one or more "inside scatterers" in a full solution region 908A-C, such as included in each of the tiles (e.g., tiles 1, 2, . . . , N) can be included in the sub-model in their unaltered (e.g., full solution) state. One or more other possible "outside" scatterers can be reduced or simplified, such as using the techniques described above, such as in a second region 912A-C, outside the full-solution region but still within the ROI. As in the temporal tiling example of FIG. 8, the inclusion of the reduced form of the outside scatterers can negate some of the computational performance gains; however, if they are reduced by a large enough margin, there can still be a reduction in overall computational complexity, especially if such techniques are used for parallelization of partitioned estimation problems. For example, the full-solution portions included in one or more tiles of the spatial tiling example of FIG. 9 can be reconstructed in parallel.

In an example, an image reconstruction on the various tiles can be performed in parallel, such as to allow distribution of the reconstruction process across multiple processors. For example, a system (e.g., the system 100 of FIG. 1) can first determine a complete reconstruction over the entire insonified region of interest, such as assuming a level of detail corresponding only to the "outside" scatterers. Such a "low quality image" can then be used to seed a higher-quality reconstruction performed in a parallel manner using both inside and outside scatterer reconstructions. For example, the "low quality" image could be used to seed "outside" regions in the reconstruction. In an example, the "low quality" image can be reprojected to form a seed (e.g., a first iteration) for reconstruction of the higher-quality "inner" regions as well. Such a tiered approach might reduce the number of iterations required for convergence, thereby speeding reconstruction.

Generally, in the examples of FIGS. 8-9, a rank reduction of array manifold matrix representing the outside scatterers using principal component analysis can be a reasonable approach to reduce computational complexity. However, it is believed that such an approach does not optimally account for the impact of those scatterers on the reconstruction of the image tile. For example, outside scatterers that are further away from the full-solution tile, in space, can have less impact on the performance of the tile reconstruction than do closer ones. Rather than reducing the outside set generally to its principal components, the present inventors have also recognized that it can be more efficient to first take into account the relative impact that a particular outside scatterer has on the tile reconstruction. In an example, system responses from every scatterer in the full model can be cross-correlated.

Then, such as before performing principal component analysis on the outside set, one or more outside scatterers' system responses can be weighted by a corresponding average (or other central tendency) of the correlation coefficient with one or more scatterers (e.g., candidate targets) within the tile. Such a correlation analysis can result in a larger share of the energy of the reduced outside set coming from those outside scatterers that have a greater impact on the tile reconstruction, such as allowing for a more compact representation of the outside scatters' corresponding model matrix. A correlation performed in this manner can, but need not, operate on complex signal representations. For example, for complex signal representations, the magnitude information can be used.

Illustrative Examples of TONE, dTONE, and qTONE

Figure 10:
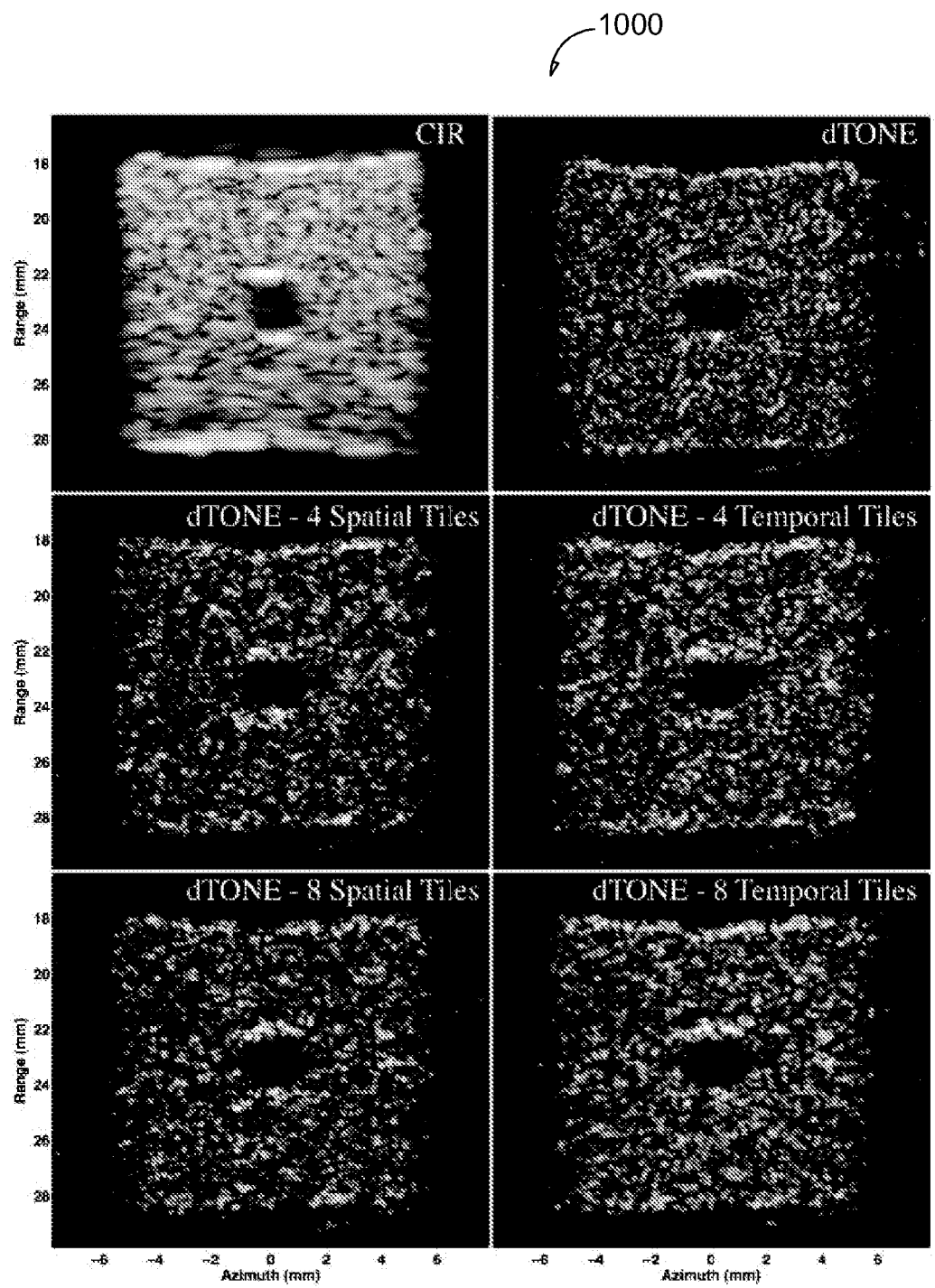
FIG. 10 includes illustrative examples of conventional image reconstruction (CIR), and diffuse time-domain estimation (dTONE), using an anechoic cyst phantom, including spatial or temporal tiling such as included in the examples of FIGS. 8-9.

FIG. 10 includes an illustrative example 1000 of comparison between conventional image reconstruction (CIR), and diffuse time-domain estimation (dTONE), such as including one or more techniques of the examples of FIGS. 2-5, including spatial or temporal tiling such as included in the examples of FIGS. 8-9.

In the illustrative example of FIG. 10, a 3 mm diameter, 7 cm long cylindrical anechoic cyst, surrounded by a 1×1×7 cm speckle-generating region was formed in 7% acrylamide gel. The 1×1×7 cm region of acrylamide gel included Sephadex™ G-50 Superfine scatterers, provided by GE Healthcare, and was embedded in a larger block of acrylamide gel containing no scatterers such that the center of the cyst was at a depth of about 2 cm from the top of the phantom. An Ultrasonix Sonix RP system including a 128 channel, 300 μm pitch, linear transducer array was used to transmit about a 6.6 MHz, 60% −6 dB fractional bandwidth plane wave and to obtain single channel RF data. The data was filtered using a 100-tap FIR filter with a pass-band from about 3-10 MHz, demodulated to produce an IQ pair, and all but the center 64 channels were removed.

In the illustrative example of FIG. 10, the array manifold matrix used for the "dTONE" images (tiled and untiled) was constructed by shifting and warping an experimentally-determined spatial response from a single 20 μm diameter stainless steel wire embedded in the same 7% acrylamide gel at a depth of about 2 cm. Elevation effects were not modeled in these illustrative examples. In the array manifold matrix, hypothetical (e.g., candidate target) scatterers were modeled every 95.6 μm axially and every 120 μm laterally. In some images included in FIG. 10, the region of interest was divided spatially and temporally into both 4 and 8 tiles as described in the examples of FIGS. 7-8, keeping 99.99% of the energy from the hypothetical scatterers outside the tiles.

For spatial tiling, the ROI was divided vertically such that all tiles spanned the full azimuthal width of the ROI. For temporal tiling, the time-channel windows were sized to overlap by 50%. Dividing the ROI spatially into 4 tiles was observed to speed up the reconstruction by a factor of 4.9, while using 8 tiles was observed speed up the reconstruction by a factor of 12.2. Despite having larger numbers of hypothetical scatterers, temporal tiling reduced the computational complexity slightly more than spatial tiling, likely due to the significantly reduced number of input samples.

For comparison, the CIR image was formed using a 64 element, 300 μm pitch aperture on both transmit and receive (e.g., the nominal configuration for the ultrasound system used). The transmit beam was focused at about 2 cm depth and dynamic receive focusing was applied after band-pass filtering and apodization with a Nuttall window. The CIR image has about −6.4 dB of cystic contrast, while the non-tiled dTONE image has about −14.4 dB of contrast. The spatially tiled dTONE images lose as much as 2.1 dB of contrast using 8 tiles while the temporally tiled images only lose 0.3 dB of contrast.

Figure 11A:
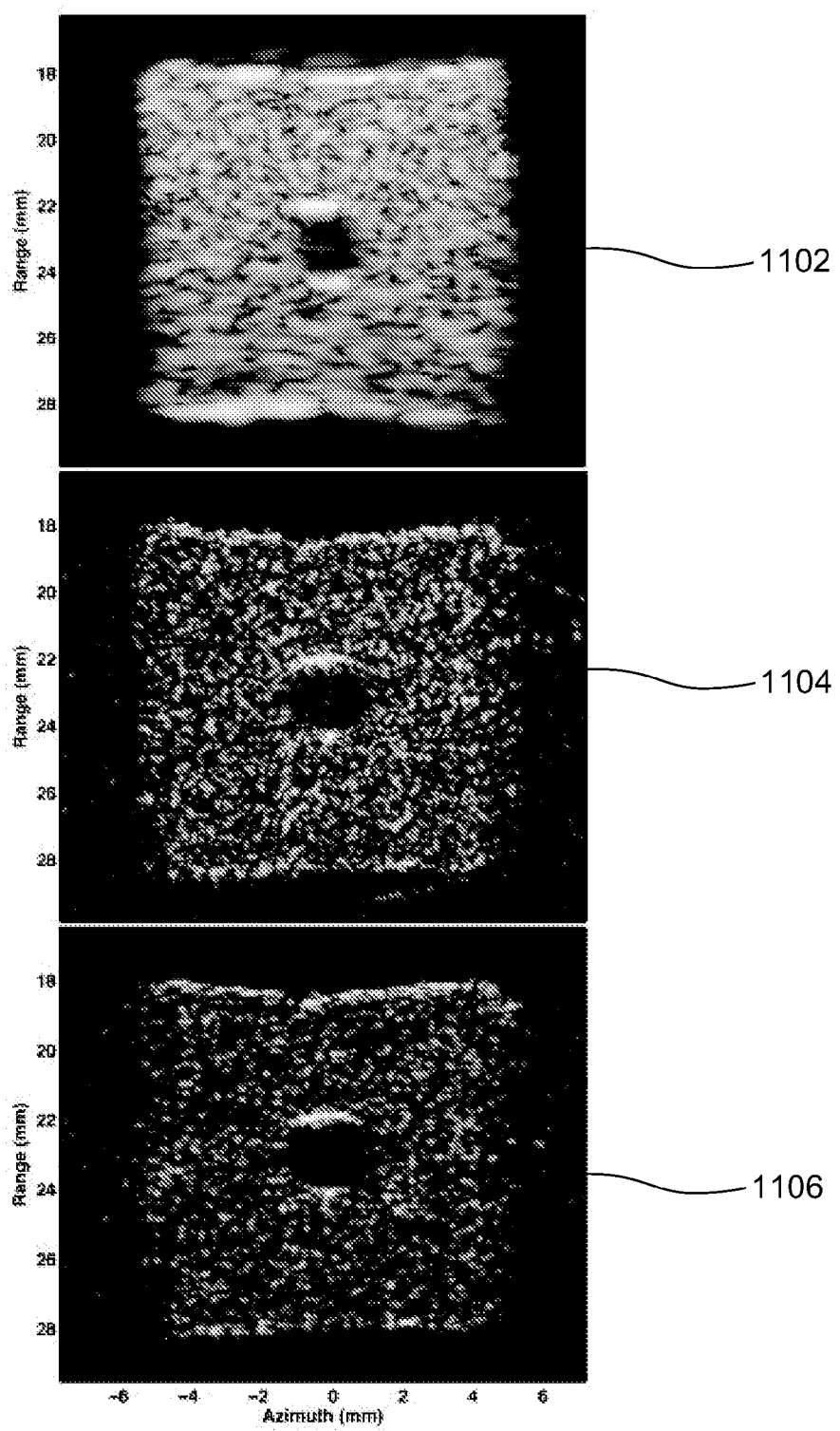
FIGS. 11A-C include illustrative examples of conventional image reconstruction (CIR), diffuse time-domain estimation (dTONE), and quick time-domain estimation (qTONE), such as using a reduced-rank system model or including downsampling.
Figure 11B:
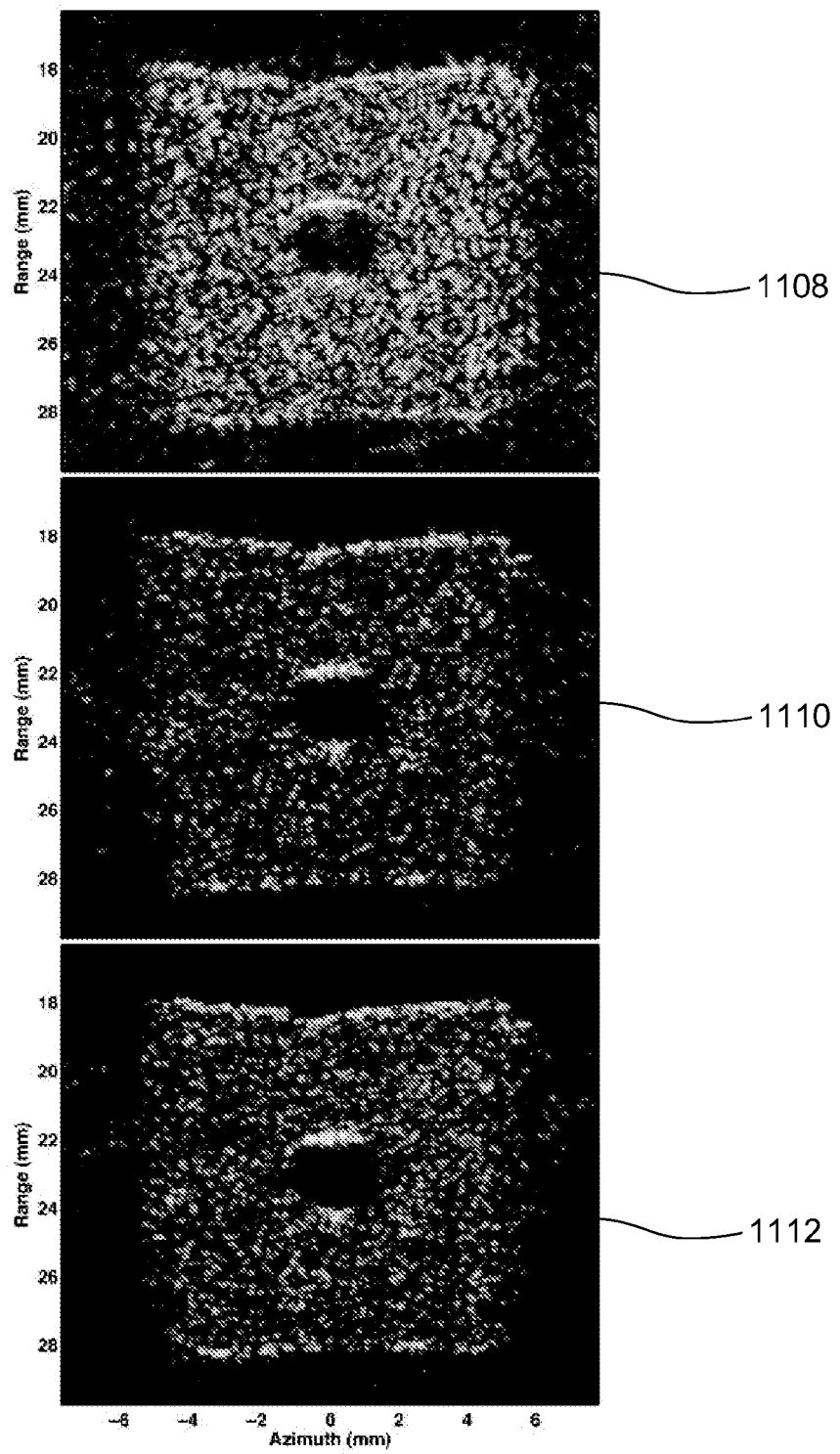
Figure 11C:
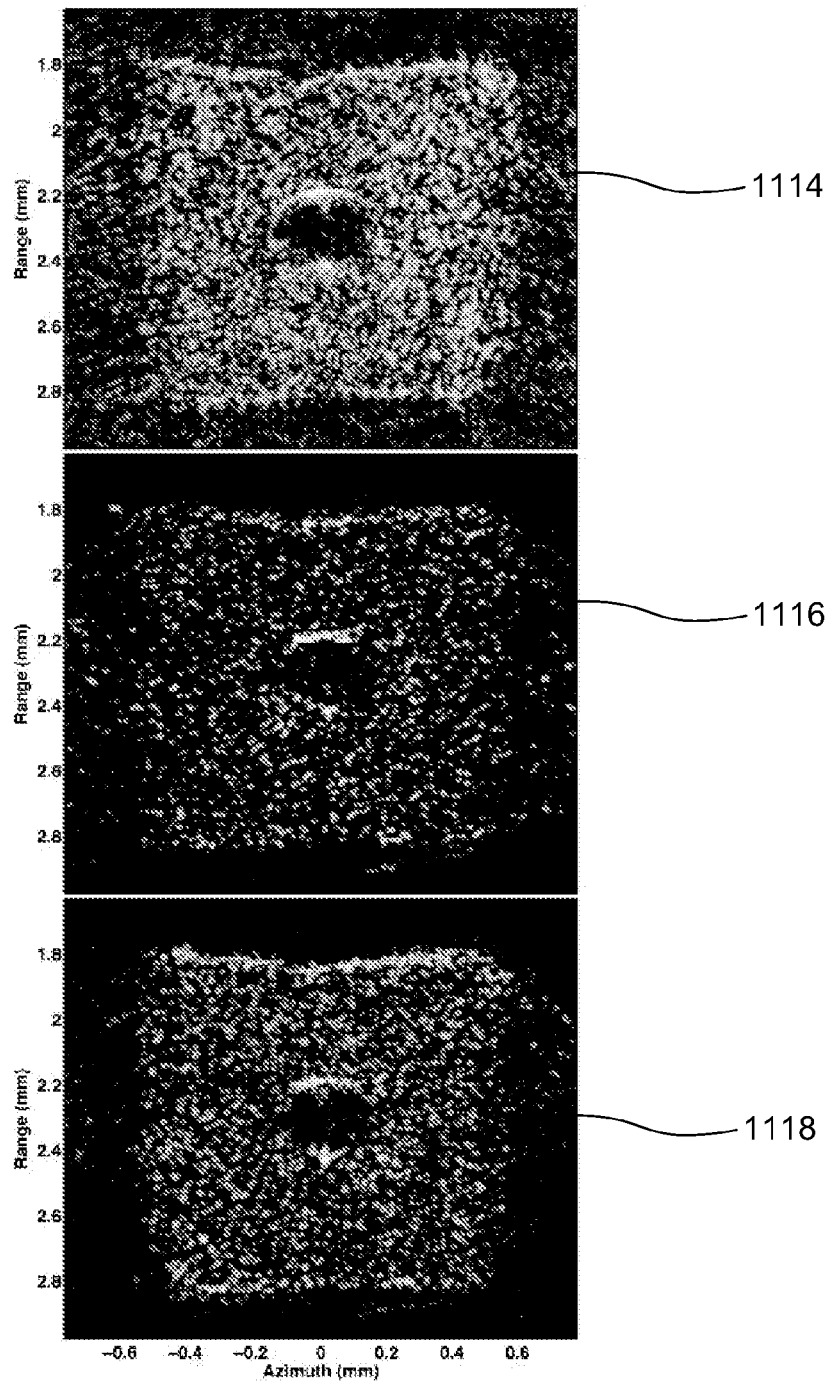

FIG. 11A includes illustrative examples of a conventional image reconstruction (CIR) 1102, a full rank 10,974 diffuse time-domain estimation (dTONE) 1104, and a full rank 13,696 quick time-domain estimation (qTONE) 1106. FIG. 11B includes a reduced rank 6848 dTONE estimation 1108, a temporally down-sampled qTONE estimation 1110, and a singular value decomposition (SVD) downsampled qTONE estimation 1112. FIG. 11C includes a reduced rank 3424 dTONE estimation 1114, a temporally-downsampled qTONE estimation 1116, and an SVD downsampled qTONE estimation. The illustrative examples of FIGS. 11A-C can be provided using one or more techniques shown in the examples of FIGS. 2-9 above.

In the illustrative examples of FIGS. 11A-C, a 3 mm diameter, 7 cm long cylindrical anechoic cyst, surrounded by a 1×1×7 cm speckle-generating region was formed in 7% acrylamide gel. The 1×1×7 cm region of acrylamide gel included Sephadex™ G-50 Superfine scatterers, provided by GE Healthcare, and was embedded in a larger block of acrylamide gel containing no scatterers such that the center of the cyst was at a depth of about 2 cm from the top of the phantom. An Ultrasonix Sonix RP system employing a 128 channel, 300 μm pitch, linear transducer array was used to transmit about a 6.6 MHz, 60% fractional bandwidth plane wave and to obtain single channel RF data. The data was filtered using a 100-tap FIR filter with a pass-band from about 3-10 MHz, demodulated to produce an IQ pair, and all but the center 64 channels were removed.

The array manifold matrix used for the dTONE and qTONE examples was constructed by shifting and warping the experimentally-determined spatial response from a single 20 μm diameter stainless steel wire embedded in the same 7% acrylamide gel at a depth of 2 cm. Elevation effects were not modeled in the illustrative examples of FIGS. 11A-C. Hypothetical targets (e.g., candidate targets) were modeled every 95.6 μm axially and every 120 μm laterally for both TONE and dTONE. This system model has dimensions 13,632×18,471 samples including a total of 10,974 "fix" eigenvectors. Images were formed with progressively smaller rank in order to assess the computation time and reconstruction performance for dTONE as compared to qTONE using both simple temporal downsampling as well as SVD rank reduction. dTONE images can be formed such as using the techniques of one or more of FIGS. 2-5, such as performed using a system as shown in the example of FIG. 1. For qTONE, the input data was downsampled temporally by a factor of two and four so that only 6,848 and 3,424 input samples were included, respectively. qTONE was also rank reduced to those same levels using the SVD method described above with respect to the examples of FIGS. 6-7.

Likewise, for dTONE, the balance between "fix" and "free" was adjusted so that only 6,848 and 3,424 eigenvectors were included in the "fix" set. In this way, the computation time and reconstruction performance of dTONE can be compared with those of the two qTONE methods at three different levels of rank reduction. qTONE, using both temporal downsampling and SVD rank reduction can achieve improved image quality and reduced computation time compared to dTONE, in the reduced rank illustrative examples. Both of the qTONE methods can achieve an additional computation cost reduction as compared to dTONE, such as about 44%, such as due to reduced memory access requirements. For example, qTONE at rank 6,848 achieves an 8.4 dB contrast improvement over full rank dTONE while also reducing the computation time by a factor of 8.

For comparison, the CIR image 1102 was formed using a 64 element, 300 μm pitch aperture on both transmit and receive (e.g., the nominal configuration for the ultrasound system used). The transmit beam was focused at about 2 cm depth and dynamic receive focusing was applied after bandpass filtering and apodization with a Nuttall window.

Figure 12:
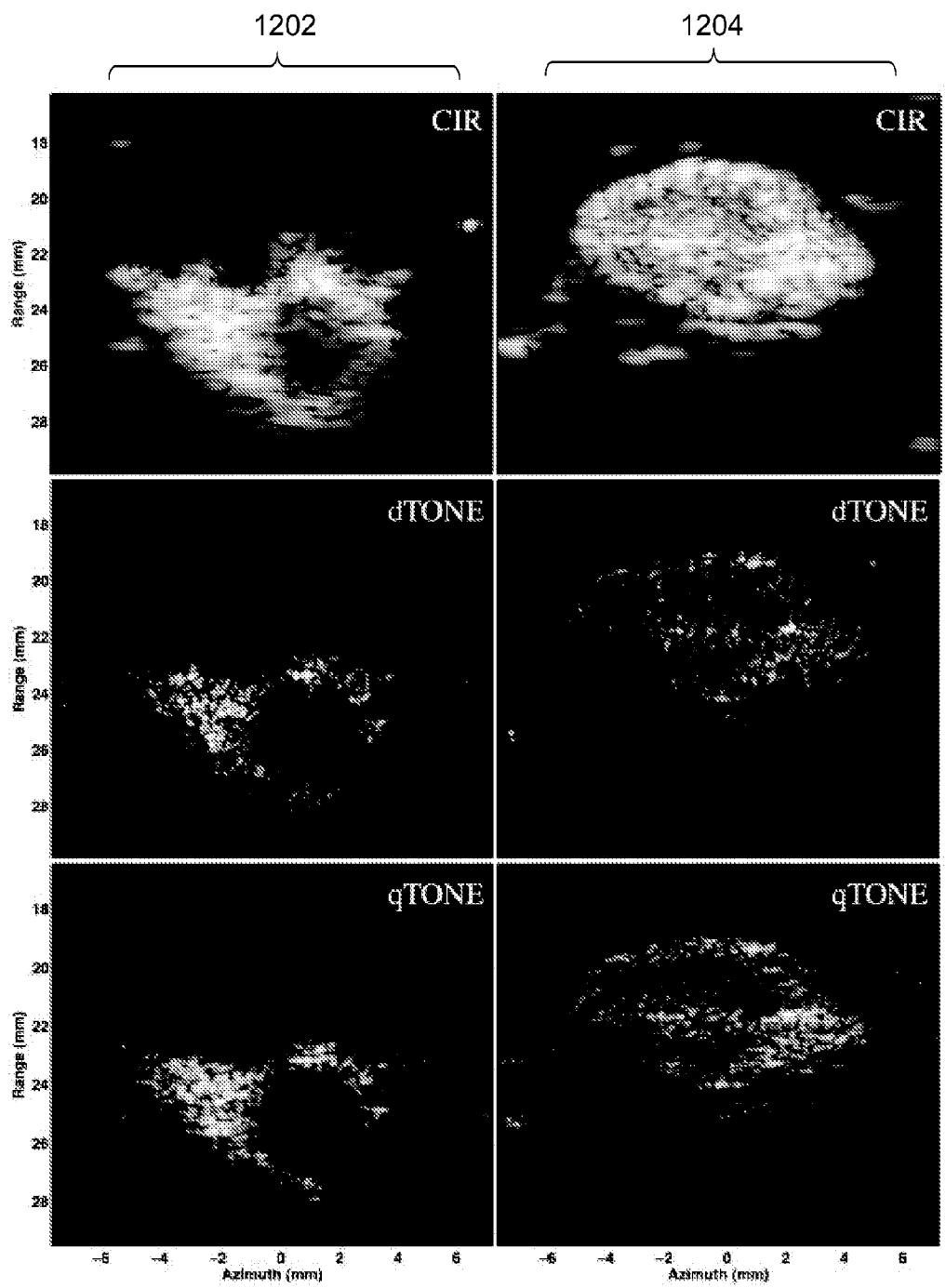
FIG. 12 includes illustrative examples of conventional image reconstruction (CIR), diffuse time-domain estimation (dTONE), and quick time-domain estimation (qTONE), using excised tissue.

FIG. 12 includes illustrative examples of conventional image reconstruction (CIR), diffuse time-domain estimation (dTONE), and quick time-domain estimation (qTONE), using excised tissue. In the illustrative examples in a second column 1204 of images, an excised mouse heart was flushed with phosphate-buffered solution (PBS) to remove any remaining blood from the chambers and then embedded at a depth of about 2 cm in a block of 7% acrylamide gel. Effort was taken to ensure the chambers of the heart remained in an open state by backfilling them with 7% acrylamide prior to embedding the heart.

In the illustrative examples of a first column 1202 of images, a 3 cm length of aorta was excised from a rabbit, flushed with PBS, and backfilled with 7% acrylamide prior to embedding it in a block of 7% acrylamide at a depth of 2 cm. Both tissue samples were then imaged using the same parameters used for the anechoic cyst phantoms similarly to the illustrative examples of FIG. 10, and FIGS. 11A-C, with dTONE operating at full rank (rank 10,974) and qTONE at rank 6,848.

Similarly to the illustrative examples of FIG. 10, and FIGS. 11A-C, elevation slice thickness was not modeled. Although both dTONE images demonstrate enhanced contrast and resolution as compared to the CIR images, delineation of tissue boundaries can still be somewhat difficult, especially in the mouse heart image. The qTONE images, however, show a superior delineation of the boundary between the septum and the anechoic ventricles due to increased contrast as compared to dTONE. In addition, the increased contrast of qTONE in the illustrative examples of FIG. 12 comes paired with an 8× reduction in computation time and a 2.7× reduction in memory requirements.

"Dithering," Such as for Speckle Reduction in an Image

Figure 13:
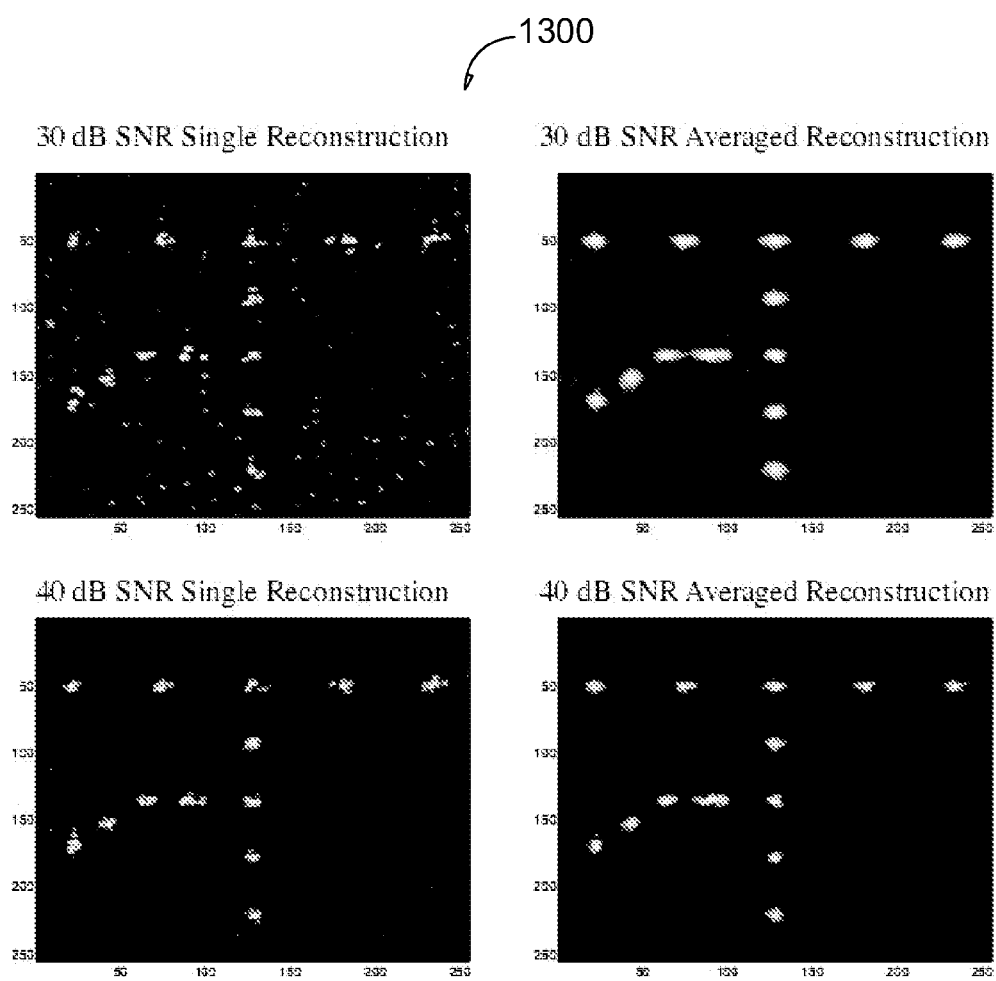
FIG. 13 includes an illustrative example of a speckle-reduction technique.

FIG. 13 includes an illustrative example 1300 of a speckle-reduction technique, including various examples of images constructed including 50 dB logarithmic compression of brightness information. In an example, one or more techniques such as including one or more of the examples shown in FIGS. 2-9 can provide an image estimating one or more actual target locations, such as including noise or speckle from one or more speckle-generating targets. In the illustrative examples of the "30 dB SNR Single Reconstruction" and "40 dB SNR Single Reconstruction" of FIG. 13, one or more point targets can provide images including a noisy appearance, similar to an ultrasound image including speckle.

In an example, one or more specified signals (e.g., a dithering signal) can be added to an echo data set, such as to perturb or "dither" the echo data, such used for reconstruction in one or more of FIGS. 2-9. One or more image constructions can be performed using the dithered echo data, and a composite or combination of such dithered constructions can be formed. For example, a first specified dithering signal and a second specified dithering signal can be represented respectively by first and second dithering vectors, and such vectors can be added to the echo data set. A first and a second corresponding image can be constructed such as using a first dithered echo data set and a second dithered echo data set, and the resulting brightness or magnitude information represented by the constructed images can be averaged (or combined using one or more other central tendencies, such as a weighted average), such as to suppress or reduce speckle, or otherwise smooth the image reconstruction.

In an example, such as when one or more of the techniques of FIGS. 2-9 are used, such as performed by a system as shown in FIG. 1, such a reconstruction need not involve determining a new covariance matrix nor iterating a full solution for each dithered echo data set. For example, a covariance matrix, or one or more other terms can be determined using a baseline of undithered echo data, and such results can be used to determine an approximate reconstruction including the specified dithering vector.

For example, similarly to the examples of FIGS. 2-9 above, an estimated vector of the weights of candidate targets can be represented by:

$$\hat{f} = C_f V^H (V C_f V^H + C_n)^{-1} x = Ex \quad \text{(EQN. 13.1)}$$

where "$C_n$" can model a noise term inherent to the echo data set (e.g., due to thermal noise in the transducer or noise generated in the electronics in the signal channel), but where no specified dithering has been added (e.g., a "baseline" reconstruction).

Then, a "dithered" reconstruction can be represented as:

$$\hat{f}_d = E(x+d) \quad \text{(EQN. 13.2)}$$

such as by adding a specified dithering vector, "d," including a specified dithering signal, to the baseline echo data set. In an example, one or more dithering vectors are random noise vectors. In an example, a set of dithering vectors can completely span the subspace, such as applied sequentially. Since the estimate $\hat{f}$ can be complex, including both magnitude and phase information, a magnitude of one dithered reconstruction can be represented by:

$$|\hat{f}_d| = |E(x+d)| = |E_x + E_d| \quad \text{(EQN. 13.3)}$$

and if the magnitude of d≪x, then EQN. 13.3 can be further approximated by:

$$|\hat{f}_d| \approx |E_x| + |E_d| \quad \text{(EQN. 13.4)}$$

where $|E_x|$ can represent the magnitude of the original "baseline" reconstruction, and $|E_d|$ can represent the magnitude contribution due to the specified dithering vector. The approximation of EQN. 13.4 can reduce the computational burden involved in the dithering process, since a full image reconstruction need not be recomputed for each dithering iteration (e.g., a covariance matrix determined for the "baseline" reconstruction can be reused, among others).

In an example, two or more constructions can be performed such as corresponding to a respective dithering vector for each reconstruction, and a composite reconstruction can be determined across the multiple dithers, such as using an average or other central tendency of the magnitudes of the dithered constructions, such as to provide an image reconstruction including less speckle than the baseline reconstruction without dithering. For example, an average reconstruction across multiple dithers (e.g., "N" dithers), can be approximated by:

$$\frac{1}{N}\sum_{i=1}^{N} |\hat{f}_{di}| \approx |E_x| + \frac{1}{N}\sum_{i=1}^{N} |E_{di}| \quad \text{(EQN. 13.5)}$$

if $E=[e_1 e_2 e_3 \ldots e_m]$ and $$d_1 = \begin{bmatrix} 1 \\ 0 \\ 0 \\ \vdots \\ 0 \end{bmatrix}, d_2 = \begin{bmatrix} 0 \\ 1 \\ 0 \\ \vdots \\ 0 \end{bmatrix}, d_3 = \begin{bmatrix} 0 \\ 0 \\ 1 \\ \vdots \\ 0 \end{bmatrix}, \ldots,$$

then EQN. 13.5 can be represented by:

$$\frac{1}{N}\sum_{i=1}^{N}|\hat{f}_{di}| = |E_x| + \frac{1}{N}\sum_{j=1}^{M}|e_j| \quad \text{(EQN. 13.6)}$$

In the illustrative examples of FIG. 13, simulations of echo data sets are included using a 30 dB SNR (e.g., the "30 dB SNR Averaged Reconstruction" included in FIG. 13), and using a 40 dB SNR (e.g., the "40 dB SNR Averaged Reconstruction" included in FIG. 13). The two simulations illustrate an averaged reconstruction including an average of multiple constructions, and each shows less noise than the corresponding single reconstructions. A similar reduction in observed speckle can be observed in actual ultrasound echo data, where the echoes created by speckle-generating targets as opposed to the point targets included in the simulations of FIG. 13.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method, comprising:

using at least one processor circuit, receiving an echo data set obtained using one or more transducers, the echo data set including information representative of an echo provided at least in part by one or more actual targets included in a region of interest;

using at least one processor circuit, modeling the region of interest, the modeling including selecting or generating an array manifold matrix, the array manifold matrix including information corresponding to any one or more candidate targets included in the region of interest;

using at least one processor circuit, adding a first specified dithering signal to the echo data set to provide a first dithered echo data set; and using at least one processor circuit, determining weights of the candidate targets using the array manifold matrix and the echo data set, the determining the weights including:

determining a first vector representing the weights of the candidate target locations using the first dithered echo data set including minimizing an argument of a function modeling the weights of the candidate targets, the minimizing subject to a constraint that a product of the array manifold matrix and the first vector representing the determined weights of each of the one or more candidate targets is about equal to the received echo data set corresponding to the one or more actual targets.

2. The method of claim 1, wherein the function modeling the weights of the candidate targets includes an exponential function.

3. The method of claim 2, wherein the function modeling the weights of the candidate targets includes a joint Gaussian probability density function.

4. The method of claim 1, wherein the minimizing argument includes using at least one processor circuit to minimize a product of (1) a Hermitian transpose of the vector representing the weights of each of the one or more candidate targets, (2) the inverse of a covariance matrix determined using the vector representation of the weights of each of the one or more candidate targets, and (3) the vector representation of the weights of each of the one or more candidate targets.

5. The method of claim 1, wherein the determining weights of the one or more candidate targets includes using at least one processor circuit to perform a singular value decomposition of the array manifold matrix and transforming the echo data set using an inverse of a matrix provided by the singular value decomposition of the array manifold matrix.

6. The method of claim 1, comprising using at least one processor circuit to construct an image representing an estimate of one or more of the actual target locations using the determined weights of the one or more candidate targets.

7. The method of claim 6, wherein a brightness of a particular location in the image is determined at least in part using the determined weights of the one or more candidate targets.

8. The method of claim 1, wherein the region of interest includes a tissue region;
wherein the echo data set includes information representative of ultrasonic energy scattered or reflected by the one or more actual targets and received by an ultrasonic transducer; and
wherein one or more of the actual target locations are within the tissue region.

9. The method of claim 1, comprising:
using at least one processor circuit, adding a second specified dithering signal to the echo data set to provide a second dithered echo data set;
wherein the determining the weights of the candidate target locations includes
determining a second vector representing the weights of the candidate target locations using the second dithered echo data set.

10. The method of claim 9, comprising using at least one processor circuit to construct an image representing an estimate of one or more of the actual target locations using the determined weights of the one or more candidate targets; and
wherein a brightness of a particular location in the image is determined at least in part using a determined weight of one or more candidate targets included in the first vector, and a determined weight of one or more candidate targets included in the second vector.

11. The method of claim 10, wherein the brightness of a particular location in the image is determined using one or more of a central tendency of a combination, a maximum, a minimum, or a specified range of values of the determined weight of one or more candidate targets included in the first vector, and the determined weight of one or more candidate targets included in the second vector.

12. The method of claim 9, wherein the first and second specified dithering signals are represented by information included in respective first and second specified dithering vectors; and
wherein the first and second dithering vectors are orthogonal to each other.

13. The method of claim 12, wherein at least one of the first or second dithering vectors are non-random.

14. The method of claim 1, wherein the array manifold matrix is selected using at least one processor circuit.

15. The method of claim 1, wherein the array manifold matrix is generated using at least one processor circuit.

16. A system comprising a processor and a processor-readable medium, the processor-readable medium comprising instructions that, when performed by the processor, cause the system to:
receive an echo data set including information representative of an echo provided at least in part by one or more actual targets included in a region of interest;
model the region of interest, including instructions that cause the system to select or generate an array manifold matrix, the array manifold matrix including information corresponding to any one or more candidate targets included in the region of interest;
add a first specified dithering signal to the echo data set to provide a first dithered echo data set;
determine weights of the candidate targets using the array manifold matrix and the echo data set, including instructions that cause the system to:
determine a first vector representing the weights of the candidate target locations using the first dithered echo data set including minimizing an argument of a function modeling the weights of the candidate targets, the minimizing subject to a constraint that a product of the array manifold matrix and the first vector representing the determined weights of each of the one or more candidate targets is about equal to the received echo data set corresponding to the one or more actual targets.

17. The system of claim 16, wherein the function modeling weights of the candidate targets includes an exponential function.

18. The system of claim 16, wherein the function modeling the weights of the candidate targets includes a joint Gaussian probability density function.

19. The system of claim 16, wherein the instructions causing the system to minimize the argument include instructions causing the system to minimize a product of (1) a Hermitian transpose of the vector representing the weights of each of the one or more candidate targets, (2) the inverse of a covariance matrix determined using the vector representation of the weights of each of the one or more candidate targets, and (3) the vector representation of the weights of each of the one or more candidate targets.

20. The system of claim 16, wherein the instructions causing the system to determine the weights of the one or more candidate targets include instructions to:
perform a singular value decomposition of the array manifold matrix; and
transform the echo data set using an inverse of a matrix provided by the singular value decomposition of the array manifold matrix.

21. The system of claim 16, wherein the processor-readable medium comprises instructions that cause the system to reconstruct an image representing an estimate of one or more of the actual target locations using the determined weights of the one or more candidate targets.

22. The system of claim 21, wherein the processor-readable medium comprises instructions that cause the system to determine a brightness of a particular location in the image at least in part using the determined weights of the one or more candidate targets.

23. The system of claim 16, wherein the region of interest includes a tissue region;
wherein the echo data set includes information representative of ultrasonic energy scattered or reflected by the one or more actual targets and received by an ultrasonic transducer array; and
wherein one or more of the actual target locations are within the tissue region.

24. The system of claim 16, wherein the processor-readable medium comprises instructions that cause the system to:
add a second specified dithering signal to the echo data set to provide a second dithered echo data set;
wherein the instructions causing the system to determine the weights of the candidate target locations include instructions to
determine a second vector representing the weights of the candidate target locations using the second dithered echo data set.

25. The system of claim 24, wherein the processor-readable medium comprises instructions that cause the system to reconstruct an image representing an estimate of one or more of the actual target locations using the determined weights of the one or more candidate targets; and
wherein a brightness of a particular location in the image is determined at least in part using a determined weight of the one or more candidate targets included in the first vector, and a determined weight of the one or more candidate targets included in the second vector.

26. The system of claim 25, wherein the brightness of a particular location in the image is determined using one or more of a central tendency of a combination, a maximum, a minimum, or a specified range of values of the determined weight of one or more candidate targets included in the first vector, and the determined weight of one or more candidate targets included in the second vector.

27. The system of claim 24, wherein the first and second specified dithering signals are represented by information included in respective first and second specified dithering vectors; and
wherein the first and second dithering vectors are orthogonal to each other.

28. The system of claim 27, wherein at least one of the first or second dithering vectors are non-random.

29. The system of claim 16, wherein the instructions include instructions to select the array manifold matrix.

30. The system of claim 16, wherein the instructions include instructions to generate the array manifold matrix.

31. A method, comprising:
using at least one processor circuit, receiving an echo data set obtained using one or more transducers, the echo data set including information representative of an echo provided at least in part by one or more actual targets included in a region of interest;
using at least one processor circuit, modeling the region of interest, the modeling including selecting or generating an array manifold matrix, the array manifold matrix including information corresponding to any one or more candidate targets included in the region of interest;
using at least one processor circuit, adding a first specified dithering signal to the echo data set to provide a first dithered echo data set;
using at least one processor circuit, adding a second specified dithering signal to the echo data set to provide a second dithered echo data set; and
using at least one processor circuit, determining weights of the candidate targets using the array manifold matrix and the echo data set, the determining the weights subject to a constraint that a product of the array manifold matrix and a vector representation of the determined weights of each of the one or more candidate targets is about equal to the received echo data set corresponding to the one or more actual targets;
wherein the determining the weights of the candidate target locations includes:
determining a first vector representing the weights of the candidate target locations using the first dithered echo data set; and
determining a second vector representing the weights of the candidate target locations using the second dithered echo data set.

32. The method of claim 31, comprising constructing an image representing an estimate of one or more of the actual target locations using the determined weights of the one or more candidate targets; and
wherein a brightness of a particular location in the image is determined at least in part using a determined weight of one or more candidate targets included in the first vector, and a determined weight of one or more candidate targets included in the second vector.

33. The method of claim 31, wherein the array manifold matrix is selected using at least one processor circuit.

34. The method of claim 31, wherein the array manifold matrix is generated using at least one processor circuit.

35. A system comprising a processor and a processor-readable medium, the processor-readable medium comprising instructions that, when performed by the processor, cause the system to:
receive an echo data set including information representative of an echo provided at least in part by one or more actual targets included in a region of interest;
model the region of interest, including instructions that cause the system to select or generate an array manifold matrix, the array manifold matrix including information corresponding to any one or more candidate targets included in the region of interest;
determine weights of the candidate targets using the array manifold matrix and the echo data set, subject to a constraint that a product of the array manifold matrix and a vector representation of the determined weights of each of the one or more candidate targets is about equal to the received echo data set corresponding to the one or more actual targets;
add a first specified dithering signal to the echo data set to provide a first dithered echo data set;
add a second specified dithering signal to the echo data set to provide a second dithered echo data set; and
wherein the instructions causing the system to determine the weights of the candidate target locations include instructions to:
determine a first vector representing the weights of the candidate target locations using the first dithered echo data set; and
determine a second vector representing the weights of the candidate target locations using the second dithered echo data set.

36. The system of claim 35, wherein the processor-readable medium comprises instructions that cause the system to reconstruct an image representing an estimate of one or more of the actual target locations using the determined weights of the one or more candidate targets; and
   wherein a brightness of a particular location in the image is determined at least in part using a determined weight of the one or more candidate targets included in the first vector, and a determined weight of the one or more candidate targets included in the second vector.

37. The system of claim 35, wherein the instructions include instructions to select the array manifold matrix.

38. The system of claim 35, wherein the instructions include instructions to generate the array manifold matrix.

* * * * *

UNITED STATES PATENT AND TRADEMARK OFFICE
CERTIFICATE OF CORRECTION

PATENT NO. : 8,818,064 B2  
APPLICATION NO. : 13/380224  
DATED : August 26, 2014  
INVENTOR(S) : Walker et al.

Page 1 of 1

It is certified that error appears in the above-identified patent and that said Letters Patent is hereby corrected as shown below:

In the specification
In column 1, line 8, delete "award number NIH 126509-101-GC11470-3135 from the" and insert
--EB005433 awarded by--, therefor Signed and Sealed this
Thirty-first Day of May, 2016

Michelle K. Lee
*Director of the United States Patent and Trademark Office*